US006858744B2

(12) United States Patent
Kath et al.

(10) Patent No.: US 6,858,744 B2
(45) Date of Patent: Feb. 22, 2005

(54) DIHYDOXYHEXANOIC ACID DERIVATIVES, THEIR INTERMEDIATES, AND METHODS OF MAKING

(75) Inventors: John C. Kath, Waterford, CT (US); Zhengong B. Li, East Lyme, CT (US); V. John Jasys, Griswold, CT (US); Frank J. Urban, Old Saybrook, CT (US)

(73) Assignee: Pfizer Inc., New York, NY (US)

( * ) Notice: Subject to any disclaimer, the term of this patent is extended or adjusted under 35 U.S.C. 154(b) by 33 days.

(21) Appl. No.: 10/431,276

(22) Filed: May 7, 2003

(65) Prior Publication Data

US 2004/0019217 A1 Jan. 29, 2004

Related U.S. Application Data

(60) Provisional application No. 60/380,694, filed on May 14, 2002, and provisional application No. 60/397,138, filed on Jul. 18, 2002.

(51) Int. Cl.[7] ..................... C07D 307/33; C07D 201/44
(52) U.S. Cl. ...................................... 549/321; 544/355
(58) Field of Search ........................... 549/321; 544/355

(56) References Cited

U.S. PATENT DOCUMENTS

| | | | | |
|---|---|---|---|---|
| 3,119,742 | A | 1/1964 | Heimlich et al. | ............. 167/82 |
| 3,492,397 | A | 1/1970 | Peters et al. | .................. 424/20 |
| 3,538,214 | A | 11/1970 | Polli et al. | ..................... 424/19 |
| 4,060,598 | A | 11/1977 | Groppenbacher et al. | ..... 424/33 |
| 4,173,626 | A | 11/1979 | Dempski et al. | .............. 424/19 |

FOREIGN PATENT DOCUMENTS

| | | | | |
|---|---|---|---|---|
| EP | 0934923 | 8/1999 | ......... | C07C/229/28 |
| WO | WO9427955 | 12/1994 | ......... | C07C/229/08 |
| WO | WO9838167 | 9/1998 | ......... | C07D/215/54 |
| WO | WO9940061 | 8/1999 | ......... | C07C/231/00 |

OTHER PUBLICATIONS

U.S. Non–Provisional Appl. No. 09/380,269, filed Feb. 26, 1997 (our Reference: PC9739A).
U.S. Non–Provisional Appl. No. 09/403,218, filed Feb. 5, 1998 (our Reference: PC10100A).
U.S. Non–Provisional Appl. No. 10/175,132, filed Jun. 18, 2002 (our Reference: PC11709A).
U.S. Non–Provisional Appl. No. 10/175,640, filed Jun. 19, 2002 (our Reference: PC11720A).
U.S. Non–Provisional Appl. No. 10/175,566, filed Jun. 17, 2002 (our Reference: PC11876A).
U.S. Non–Provisional Appl. No. 10/173,987, filed Jun. 17, 2002 (our Reference: PC23062A).
Coligan, J. E., et al., *Current Protocols in Immunology*, 6.12.1–6.12.3, (1991).
Jasys, V. J., et al., *Tetrahedron:Asymmetry, Observation of a new dimeric amino acid derivative in the reaction of methyl N–BOC–(S)–(3–fluorophenyl)alanate with DIBAL–H and lithio ethyl propiolate*, vol. 12, pp. 361–363 (2001).
Diederich, A. M., et al., *Tetrahedron Letters, Stereoselective Synthesis of a Hydroxyethylene Dipeptide Isostere*, vol. 34, No. 39, pp. 6169–6172, (1993).
Liu, J., et al., *Tetrahedron Letters, Improved syntheses of α–BOC–amino–Weinreb amides using a pre–deprotonation protocol*, vol. 43, pp. 8223–8226, (2002).
Bailey, W. F., et al. *Organic Letters, Grignard reactions of 4–substituted–2–keto–1,3–dioxanes: Highly diasteroselective additions controlled by a remote alkyl group*, vol. 3, No. 12, pp. 1865–1868, (2001).
Benedetti, F., et al., *Tetrahedron Letters, Facile inversion of configuration of N–BOC–β–aminoalcohols via $S_N2$ cyclization to oxazolidinones*, vol. 41, pp. 10071–10074, (2000).
Yamauchi, M., *Chem. Pharm. Bull., Facile Conversion of Acetals to Nitriles*, vol. 41, No. 11, pp. 2042–2043, (1993).
Fray, A. H. et al., *J. Org. Chem., A Short, Stereoselective Synthesis of the Lactone Precursor to 2R,4S,5S Hydroxyethylene Dipeptide Isosteres*, vol. 51, pp. 4828–4833, (1986).
Ghosh, A. K., *J. Am. Chem. Soc., Design of Potent Inhibitors for Human Brain Memapsin 2 (β–Secretase)*, vol. 1222, pp. 3522–3523, (2000).
Mendre, C., *Tetrahedron, Peptide and Pseudopeptide Analogues of Cholecystokinin, Chemical Modifications of the $MET^{28}$–$GLY^{29}$ Region*, vol. 44, No. 14, pp. 4415–4430 (1988).

*Primary Examiner*—Bernard Dentz
(74) *Attorney, Agent, or Firm*—Peter C. Richardson; Gregg C. Benson; Christopher J. Verni

(57) ABSTRACT

This invention relates to dihydroxyhexanoic acid derivatives and their intermediates, as well as to methods of preparing such compounds. Additionally, present invention relates to removing a protecting group from a protected amine wherein the method comprises reacting the protected amine with phosphoric acid.

11 Claims, No Drawings

DIHYDOXYHEXANOIC ACID DERIVATIVES, THEIR INTERMEDIATES, AND METHODS OF MAKING

CROSS-REFERENCE TO RELATED APPLICATION

This application claims the benefit of priority of provisional Patent Application Ser. No. 60/380,694 filed May 14, 2002, and provisional Patent Application Ser. No. 60/397,138 filed Jul. 18, 2002, which is incorporated herein by reference in their entirety for all purposes.

FIELD OF THE INVENTION

This invention relates to dihydroxyhexanoic acid derivatives and their intermediates, as well as to methods of preparing such compounds.

BACKGROUND

Dihydroxyhexanoic acid derivatives are potent and selective inhibitors of MIP-1α, binding to the receptor CCR1 found on inflammatory and immunomodulatory cells (preferably leukocytes and lymphocytes). The CCR1 receptor is also sometimes referred to as the CC-CKR1 receptor. These compounds also inhibit MIP-1α (and the related chemokine shown to interact with CCR1 (e.g., RANTES and MCP-3)) induced chemotaxis of THP-1 cells and human leukocytes and are potentially useful for the treatment or prevention of autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult Respiratory Distress Syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), transplantation tissue rejection (chronic and acute), organ rejection (chronic and acute), atherosclerosis, restenosis, HIV infectivity (co-receptor usage), and granulomatous diseases (including sarcoidosis, leprosy and tuberculosis).

Dihydroxyhexanoic acid derivatives are described in co-pending U.S. patent application Ser. No. 09/380,269, filed Feb. 5, 1998 and Ser. No. 09/403,218, filed Jan. 18, 1999; and PCT publication numbers WO98/38167 and WO99/40061, commonly assigned to the assignee of the present invention and all of which are incorporated herein by reference in their entireties for all purposes.

SUMMARY OF THE INVENTION

As embodied and broadly described herein, this invention, in one aspect, relates to methods of making compounds of the formula (IIIa1-1)

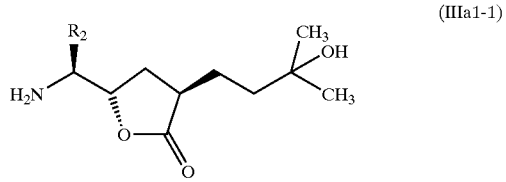

wherein:

$R_2$ is phenyl-$(CH_2)_m$—, naphthyl-$(CH_2)_m$—, $(C_3-C_{10})$cycloalkyl-$(CH_2)_m$, $(C_1-C_6)$alkyl or $(C_2-C_9)$heteroaryl-$(CH_2)_m$—, wherein each of said phenyl, naphthyl, $(C_3-C_{10})$cycloalkyl or $(C_2-C_9)$heteroaryl moieties of said phenyl-$(CH_2)_m$—, naphthyl-$(CH_2)_m$—, $(C_3-C_{10})$cycloalkyl-$(CH_2)_m$— or $(C_2-C_9)$heteroaryl-$(CH_2)_m$ — groups may optionally be substituted with one, two, or three substituents independently selected from the group consisting of hydrogen, halogen, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, [$(C_1-C_6)$alkyl]$_2$ amino, amino$(C_1-C_6)$alkyl, $(C_1-C_6)$alkylamino$(C_1-C_6)$alkyl, [$(C_1-C_6)$alkyl]$_2$amino$(C_1-C_6)$alkyl, $H_2N$—(C=O)—, $(C_1-C_6)$alkyl-NH—(C=O)—, [$(C_1-C_6)$alkyl]$_2$ N—(C=O)—, $H_2N$(C=O)—$(C_1-C_6)$alkyl, $(C_1-C_6)$alkyl-HN(C=O)—$(C_1-C_6)$alkyl, [$(C_1-C_6)$alkyl]$_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, [$(C_1-C_6)$alkyl]$_2$N—$SO_2$—$(C_1-C_6)$alkyl, $CF_3SO_3$—, $(C_1-C_6)$alkyl-$SO_3$—, phenyl, phenoxy, benzyloxy, $(C_3-C_{10})$cycloalkyl, $(C_2-C_9)$heterocycloalkyl, and $(C_2-C_9)$heteroaryl; and m is 0, 1, 2, 3, or 4 wherein the method comprises reacting a compound of the formula (IVa1-1)

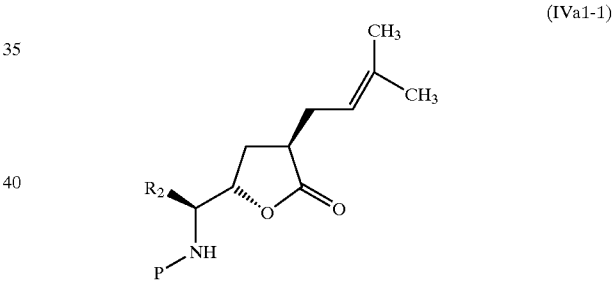

wherein P is a protecting group, with phosphoric acid.

In the methods and compounds herein described, the variables shall have the same definition unless otherwise noted.

A second aspect of the present invention relates to methods of making compounds of the formula (IIa1-1)

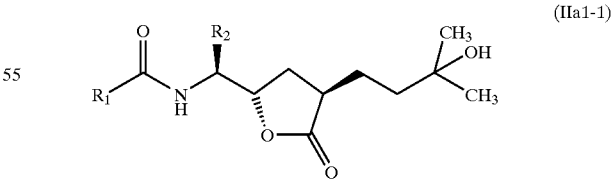

wherein $R_1$ is $(C_2-C_9)$heteroaryl optionally substituted with one, two or three substituents independently selected from the group consisting of hydrogen, halogen, cyano, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino $(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, $H_2N$—SO$_2$—, $H_2N$—SO$_2$—$(C_1-C_6)$alkyl, $(C_1-C_6)$alkylHN—SO$_2$—$(C_1-C_6)$alkyl, $[(C_1-C_6)$alkyl$]_2N$—SO$_2$—$(C_1-C_6)$alkyl, $CF_3SO_3$—, $(C_1-C_6)$alkyl-SO$_3$—, phenyl, $(C_3-C_{10})$cycloalkyl, $(C_2-C_9)$heterocycloalkyl, and $(C_2-C_9)$heteroaryl;

$R_2$ is phenyl-$(CH_2)_m$—, naphthyl-$(CH_2)_m$—, $(C_3-C_{10})$cycloalkyl-$(CH_2)_m$—, $(C_1-C_6)$alkyl or $(C_2-C_9)$heteroaryl-$(CH_2)_m$—, wherein each of said phenyl, naphthyl, $(C_3-C_{10})$cycloalkyl or $(C_2-C_9)$heteroaryl moieties of said phenyl-$(CH_2)_m$—, naphthyl-$(CH_2)_m$—, $(C_3-C_{10})$cycloalkyl-$(CH_2)_m$— or $(C_2-C_9)$heteroaryl-$(CH_2)_m$— groups may optionally be substituted with one, two, or three substituents independently selected from the group consisting of hydrogen, halogen, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—H—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, $H_2N$—SO$_2$—, $H_2N$—SO$_2$—$(C_1-C_6)$alkyl, $(C_1-C_6)$alkylHN—SO$_2$—$(C_1-C_6)$alkyl, $[(C_1-C_6)$alkyl$]_2N$—SO$_2$—$(C_1-C_6)$alkyl, $CF_3SO_3$—, $(C_1-C_6)$alkyl-SO$_3$—, phenyl, phenoxy, benzyloxy, $(C_3-C_{10})$cycloalkyl, $(C_2-C_9)$heterocycloalkyl, and $(C_2-C_9)$heteroaryl; and m is 0, 1, 2, 3, or 4 wherein the method comprises:

a) reacting a compound of the formula (IVa1-1)

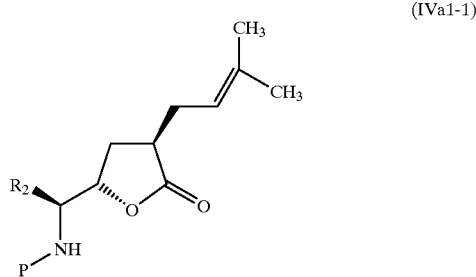

(IVa1-1)

wherein P is a protecting group, with phosphoric acid to form a compound of the formula (IIIa1-1)

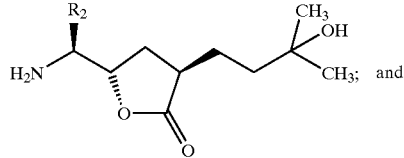

(IIIa1-1)

b) coupling the compound of the formula (IIIa1-1) so formed with a compound having the formula $R_1$—CO—X, wherein X is hydroxy or halogen.

A third aspect of the present invention relates to methods of making compounds of the formula (Ia-1)

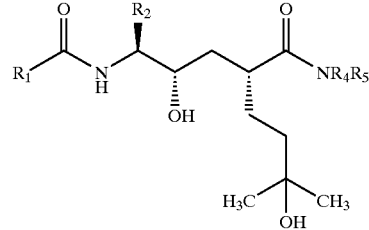

(Ia-1)

wherein:

$R_1$ is $(C_2-C_9)$heteroaryl optionally substituted with one, two or three substituents independently selected from the group consisting of hydrogen, halogen, cyano, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, $H_2N$—SO$_2$—, $H_2N$—SO$_2$—$(C_1-C_6)$alkyl, $(C_1-C_6)$alkylHN—SO$_2$—$(C_1-C_6)$alkyl, $[(C_1-C_6)$alkyl$]_2N$—SO$_2$—$(C_1-C_6)$alkyl, $CF_3SO_3$—, $(C_1-C_6)$alkyl-SO$_3$—, phenyl, $(C_3-C_{10})$cycloalkyl, $(C_2-C_9)$heterocycloalkyl, and $(C_2-C_9)$heteroaryl;

$R_2$ is phenyl-$(CH_2)_m$—, naphthyl-$(CH_2)_m$—, $(C_3-C_{10})$cycloalkyl-$(CH_2)_m$—, $(C_1-C_6)$alkyl or $(C_2-C_9)$heteroaryl-$(CH_2)_m$—, wherein each of said phenyl, naphthyl, $(C_3-C_{10})$cycloalkyl or $(C_2-C_9)$heteroaryl moieties of said phenyl-$(CH_2)_m$—, naphthyl-$(CH_2)_m$—, $(C_3-C_{10})$cycloalkyl-$(CH_2)_m$— or $(C_2-C_9)$heteroaryl-$(CH_2)_m$— groups may optionally be substituted with one, two, or three substituents independently selected from the group consisting of hydrogen, halogen, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$ alkyl, NO$_2$, amino, (C$_1$–C$_6$)alkylamino, [(C$_1$–C$_6$)alkyl]$_2$ amino, amino(C$_1$–C$_6$)alkyl, (C$_1$–C$_6$)alkylamino(C$_1$–C$_6$) alkyl, [(C$_1$–C$_6$)alkyl]$_2$amino(C$_1$–C$_6$)alkyl, H$_2$N—(C=O)—, (C$_1$–C$_6$)alkyl-NH—(C=O)—, [(C$_1$–C$_6$)alkyl]$_2$N—(C=O)—, H$_2$N(C=O)—(C$_1$–C$_6$)alkyl, (C$_1$–C$_6$)alkyl-HN(C=O)—(C$_1$–C$_6$)alkyl, [(C$_1$–C$_6$)alkyl]$_2$N—(C=O)—(C$_1$–C$_6$)alkyl, H(O=C)—NH—, (C$_1$–C$_6$)alkyl(C=O)—NH, (C$_1$–C$_6$)alkyl(C=O)—[NH](C$_1$–C$_6$)alkyl, (C$_1$–C$_6$)alkyl(C=O)—[N(C$_1$–C$_6$)alkyl](C$_1$–C$_6$)alkyl, (C$_1$–C$_6$)alkyl-S—, (C$_1$–C$_6$)alkyl-(S=O)—, (C$_1$–C$_6$)alkyl-SO$_2$—, (C$_1$–C$_6$)alkyl-SO$_2$—NH—, H$_2$N—SO$_2$—, H$_2$N—SO$_2$—(C$_1$–C$_6$)alkyl, (C$_1$–C$_6$)alkylHN—SO$_2$—(C$_1$–C$_6$)alkyl, [(C$_1$–C$_6$)alkyl]$_2$N—SO$_2$—(C$_1$–C$_6$)alkyl, CF$_3$SO$_3$—, (C$_1$–C$_6$)alkyl-SO$_3$—, phenyl, phenoxy, benzyloxy, (C$_3$–C$_{10}$)cycloalkyl, (C$_2$–C$_9$)heterocycloalkyl, and (C$_2$–C$_9$)heteroaryl;

R$_4$ is hydrogen, (C$_1$–C$_6$)alkyl, hydroxy, (C$_1$–C$_6$)alkoxy, hydroxy(C$_1$–C$_6$)alkyl, (C$_1$–C$_6$)alkoxy(C=O)—, (C$_3$–C$_{10}$)cycloalkyl-(CH$_2$)$_q$—, (C$_2$–C$_9$)heterocycloalkyl-(CH$_2$)$_q$—, (C$_2$–C$_9$)heteroaryl-(CH$_2$)$_q$—, phenyl-(CH$_2$)$_q$—, or naphthyl-(CH$_2$)$_q$—; wherein said (C$_2$–C$_9$)heterocycloalkyl, (C$_2$–C$_9$)heteroaryl, phenyl and naphthyl groups may be optionally substituted with one or two substituents from the group consisting of hydrogen, halogen, cyano, (C$_1$–C$_6$) alkyl, hydroxy, hydroxy-(C$_1$–C$_6$)alkyl, (C$_1$–C$_6$)alkoxy, (C$_1$–C$_6$)alkoxy(C$_1$–C$_6$)alkyl, HO—(C=O)—, (C$_1$–C$_6$) alkyl-O—(C=O)—, HO—(C=O)—(C$_1$–C$_6$)alkyl, (C$_1$–C$_6$)alkyl-O—(C=O)—(C$_1$–C$_6$)alkyl, (C$_1$–C$_6$)alkyl-(C=O)—O—, (C$_1$–C$_6$)alkyl-(C=O)—O—(C$_1$–C$_6$)alkyl, H(O=C)—, H(O=C)—(C$_1$–C$_6$)alkyl, (C$_1$–C$_6$)alkyl (O=C)—, (C$_1$–C$_6$)alkyl(O=C)—(C$_1$–C$_6$)alkyl, NO$_2$, amino, (C$_1$–C$_6$)alkylamino, [(C$_1$–C$_6$)alkyl]$_2$ amino, amino (C$_1$–C$_6$)alkyl, (C$_1$–C$_6$)alkylamino (C$_1$–C$_6$)alkyl, [(C$_1$–C$_6$) alkyl]$_2$amino(C$_1$–C$_6$)alkyl, H$_2$N—(C=O)—, (C$_1$–C$_6$)alkyl-NH—(C=O)—, [(C$_1$–C$_6$)alkyl]$_2$N—(C=O)—, H$_2$N (C=O)—(C$_1$–C$_6$)alkyl, (C$_1$–C$_6$)alkyl-HN(C=O)—(C$_1$–C$_6$)alkyl, [(C$_1$–C$_6$)alkyl]$_2$N—(C=O)—(C$_1$–C$_6$)alkyl, H(O=C)—NH—, (C$_1$–C$_6$)alkyl(C=O)—NH, (C$_1$–C$_6$) alkyl(C=O)—[NH](C$_1$–C$_6$)alkyl, (C$_1$–C$_6$)alkyl(C=O)—[N(C$_1$–C$_6$)alkyl](C$_1$–C$_6$)alkyl, (C$_1$–C$_6$)alkyl-S—, (C$_1$–C$_6$) alkyl-(S=O)—, (C$_1$–C$_6$)alkyl-SO$_2$—, (C$_1$–C$_6$)alkyl-SO$_2$—NH—, H$_2$N—SO$_2$—, H$_2$N—SO$_2$—(C$_1$–C$_6$)alkyl, (C$_1$–C$_6$) alkylHN—SO$_2$—(C$_1$–C$_6$)alkyl, [(C$_1$–C$_6$)alkyl]$_2$N—SO$_2$—(C$_1$–C$_6$)alkyl, CF$_3$SO$_3$—, (C$_1$–C$_6$)alkyl-SO$_3$, phenyl, (C$_3$–C$_{10}$)cycloalkyl, (C$_2$–C$_9$)heterocycloalkyl, and (C$_2$–C$_9$)heteroaryl;

R$_5$ is hydrogen, (C$_1$–C$_6$)alkyl or amino; or

R$_4$ and R$_5$ together with the nitrogen atom to which they are attached form a (C$_2$–C$_9$)heterocycloalkyl group optionally substituted with one or two substituents selected from the group consisting of hydrogen, halogen, cyano, (C$_1$–C$_6$) alkyl, hydroxy, hydroxy-(C$_1$–C$_6$)alkyl, (C$_1$–C$_6$)alkoxy, (C$_1$–C$_6$)alkoxy(C$_1$–C$_6$)alkyl, HO—(C=O)—, (C$_1$–C$_6$) alkyl-O—(C=O)—, HO—(C=O)—(C$_1$–C$_6$)alkyl, (C$_1$–C$_6$)alkyl-O—(C=O)—(C$_1$–C$_6$)alkyl, (C$_1$–C$_6$)alkyl-(C=O)—O—, (C$_1$–C$_6$)alkyl-(C=O)—O—(C$_1$–C$_6$)alkyl, H(O=C)—, H(O=C)—(C$_1$–C$_6$)alkyl, (C$_1$–C$_6$)alkyl (O=C)—, (C$_1$–C$_6$)alkyl(O=C)—(C$_1$–C$_6$)alkyl, NO$_2$, amino, (C$_1$–C$_6$)alkylamino, [(C$_1$–C$_6$)alkyl]$_2$ amino, amino (C$_1$–C$_6$)alkyl, (C$_1$–C$_6$)alkylamino (C$_1$–C$_6$)alkyl, [(C$_1$–C$_6$) alkyl]$_2$amino(C$_1$–C$_6$)alkyl, H$_2$N—(C=O)—, (C$_1$–C$_6$)alkyl-NH—(C=O)—, [(C$_1$–C$_6$)alkyl]$_2$N—(C=O)—, H$_2$N (C=O)—(C$_1$–C$_6$)alkyl, (C$_1$–C$_6$)alkyl-HN(C=O)—(C$_1$–C$_6$)alkyl, [(C$_1$–C$_6$)alkyl]$_2$N—(C=O)—(C$_1$–C$_6$)alkyl, H(O=C)—NH—, (C$_1$–C$_6$)alkyl(C=O)—NH, (C$_1$–C$_6$) alkyl(C=O)—[NH](C$_1$–C$_6$)alkyl, (C$_1$–C$_6$)alkyl(C=O)—[N(C$_1$–C$_6$)alkyl](C$_1$–C$_6$)alkyl, (C$_1$–C$_6$)alkyl-S—, (C$_1$–C$_6$) alkyl-(S=O)—, (C$_1$–C$_6$)alkyl-SO$_2$—, (C$_1$–C$_6$)alkyl-SO$_2$—NH—, H$_2$N—SO$_2$—, H$_2$N—SO$_2$—(C$_1$–C$_6$)alkyl, (C$_1$–C$_6$) alkylHN—SO$_2$—(C$_1$–C$_6$)alkyl, [(C$_1$–C$_6$)alkyl]$_2$N—SO$_2$—(C$_1$–C$_6$)alkyl, CF$_3$SO$_3$—, (C$_1$–C$_6$)alkyl-SO$_3$—, phenyl, (C$_3$–C$_{10}$)cycloalkyl, (C$_2$–C$_9$)heterocycloalkyl, and (C$_2$–C$_9$) heteroaryl;

m is 0, 1, 2, 3, or 4; and q is 0, 1, 2, 3, or 4;

wherein the method comprises:

a) reacting a compound of the formula (IVa1-1)

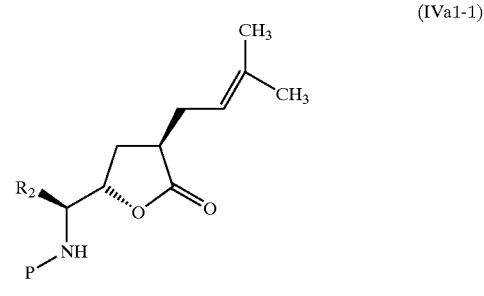

(IVa1-1)

wherein P is a protecting group, with phosphoric acid to form a compound of the formula (IIIa1-1)

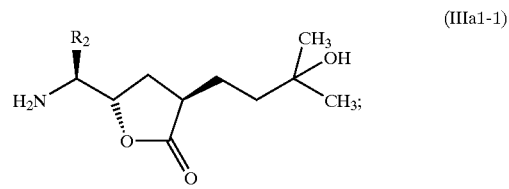

(IIIa1-1)

b) coupling the compound of the formula (IIIa1-1) so formed with a compound having the formula R$_1$—CO—X, wherein X is hydroxy or halogen, to form a compound of the formula (IIa1-1)

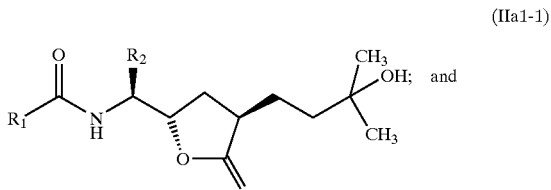

(IIa1-1)

c) reacting the compound of the formula (IIa1-1) so formed with an amine having a formula NHR$_4$R$_5$.

In a fourth aspect, the present invention relates to methods of making compounds of the formula (IVa2-1)

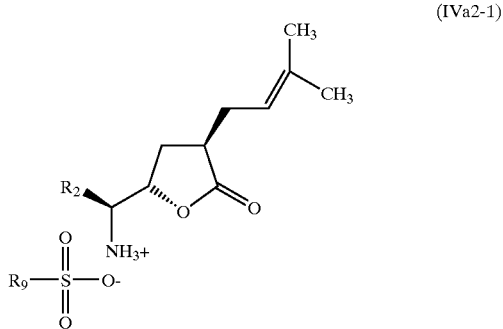

(IVa2-1)

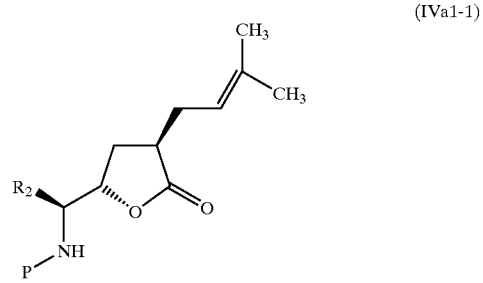

(IVa1-1)

wherein P is a protecting group, with a compound of the formula $R_9$—$SO_2$—OH.

In a fifth aspect, the present invention relates to methods of making compounds of the formula (IIIa2-1)

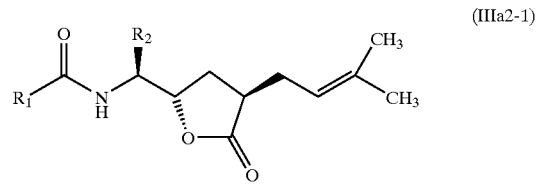

(IIIa2-1)

wherein:

$R_1$ is $(C_2-C_9)$heteroaryl optionally substituted with one, two or three substituents independently selected from the group consisting of hydrogen, halogen, cyano, $(C_1-C_6)$ alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$ alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl (O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino $(C_1-C_6)$alkyl, $(C_1-C_6)$alkylamino$(C_1-C_6)$alkyl, $[(C_1-C_6)$ alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$ (C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$ alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$ alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$ alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$ heteroaryl;

$R_2$ is phenyl-$(CH_2)_m$—, naphthyl-$(CH_2)_m$—, $(C_3-C_{10})$ cycloalkyl-$(CH_2)_m$—, $(C_1-C_6)$alkyl or $(C_2-C_9)$heteroaryl-$(CH_2)_m$—, wherein each of said phenyl, naphthyl, $(C_3-C_{10})$ cycloalkyl or $(C_2-C_9)$heteroaryl moieties of said phenyl-$(CH_2)_m$—, naphthyl-$(CH_2)_m$—, $(C_3-C_{10})$cycloalkyl-$(CH_2)_m$ — or $(C_2-C_9)$heteroaryl-$(CH_2)_m$— groups may optionally be substituted with one, two, or three substituents independently selected from the group consisting of hydrogen, halogen, CN, $(C_1-C_6)$alkyl, hydroxy, hydroxy-$(C_1-C_6)$ alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$ wherein:

$R_2$ is phenyl-$(CH_2)_m$—, naphthyl-$(CH_2)_m$—, $(C_3-C_{10})$ cycloalkyl-$(CH_2)_m$—, $(C_1-C_6)$alkyl or $(C_2-C_9)$heteroaryl-$(CH_2)_m$—, wherein each of said phenyl, naphthyl, $(C_3-C_{10})$ cycloalkyl or $(C_2-C_9)$heteroaryl moieties of said phenyl-$(CH_2)_m$—, naphthyl-$(CH_2)_m$—, $(C_3-C_{10})$cycloalkyl-$(CH_2)_m$ — or $(C_2-C_9)$heteroaryl-$(CH_2)_m$ — groups may optionally be substituted with one, two, or three substituents independently selected from the group consisting of hydrogen, halogen, CN, $(C_1-C_6)$alkyl, hydroxy, hydroxy-$(C_1-C_6)$alkyl, $(C_1-C_6)$alkoxy, $(C_1-C_6)$ alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$ alkylamino, $[(C_1-C_6)$alkyl$]_2$ amino, amino$(C_1-C_6)$alkyl, $(C_1-C_6)$alkylamino$(C_1-C_6)$alkyl, $[(C_1-C_6)$alkyl$]_2$amino $(C_1-C_6)$alkyl, $H_2N$—(C=O)—, $(C_1-C_6)$alkyl-NH—(C=O)—, $[(C_1-C_6)$alkyl$]_2$ N—(C=O)—, $H_2N(C=O)$—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$ alkyl, $CF_3SO_3$—, $(C_1-C_6)$alkyl-$SO_3$—, phenyl, phenoxy, benzyloxy, $(C_3-C_{10})$cycloalkyl, $(C_2-C_9)$heterocycloalkyl, and $(C_2-C_9)$heteroaryl;

$R_9$ is and is phenyl, naphthyl, $(C_3-C_{10})$cycloalkyl, $(C_1-C_6)$alkyl or $(C_2-C_9)$heteroaryl, wherein each of said phenyl, naphthyl, $(C_3-C_{10})$cycloalkyl or $(C_2-C_9)$heteroaryl groups may optionally be substituted with one, two, or three substituents independently selected from the group consisting of halogen, cyano, and $(C_1-C_6)$alkyl; and m is 0, 1, 2, 3, or 4;

wherein the method comprises reacting a compound of the formula (IVa1-1)

alkyl, NO₂, amino, (C₁–C₆)alkylamino, [(C₁–C₆)alkyl]₂ amino, amino(C₁–C₆)alkyl, (C₁–C₆)alkylamino(C₁–C₆) alkyl, [(C₁–C₆)alkyl]₂amino(C₁–C₆)alkyl, H₂N—(C=O)—, (C₁–C₆)alkyl-NH—(C=O)—, [(C₁–C₆)alkyl]₂N—(C=O)—, H₂N(C=O)—(C₁–C₆)alkyl, (C₁–C₆)alkyl-HN(C=O)—(C₁–C₆)alkyl, [(C₁–C₆)alkyl]₂N—(C=O)—(C₁–C₆)alkyl, H(O=C)—NH—, (C₁–C₆)alkyl(C=O)—NH, (C₁–C₆)alkyl(C=O)—[NH](C₁–C₆)alkyl, (C₁–C₆)alkyl(C=O)—[N(C₁–C₆)alkyl](C₁–C₆)alkyl, (C₁–C₆)alkyl-S—, (C₁–C₆)alkyl-(S=O)—, (C₁–C₆)alkyl-SO₂—, (C₁–C₆)alkyl-SO₂—NH—, H₂N—SO₂—, H₂N—SO₂-(C₁–C₆)alkyl, (C₁–C₆)alkylHN—SO₂—(C₁–C₆)alkyl, [(C₁–C₆)alkyl]₂N—SO₂—(C₁–C₆)alkyl, CF₃SO₃—, (C₁–C₆)alkyl-SO₃—, phenyl, phenoxy, benzyloxy, (C₃–C₁₀)cycloalkyl, (C₂–C₉)heterocycloalkyl, and (C₂–C₉)heteroaryl; and m is 0, 1, 2, 3, or 4 wherein the method comprises:

a) reacting a compound of the formula (IVa1-1)

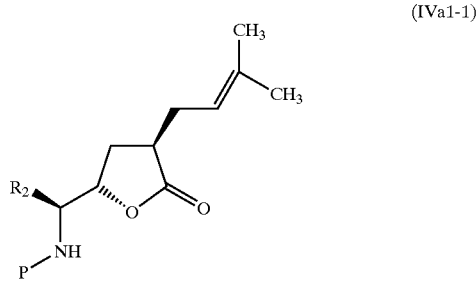

(IVa1-1)

wherein P is a protecting group, with a compound of the formula R₉—SO₂—OH wherein R₉ is and is phenyl, naphthyl, (C₃–C₁₀)cycloalkyl, (C₁–C₆)alkyl or (C₂–C₉)heteroaryl, wherein each of said phenyl, naphthyl, (C₃–C₁₀)cycloalkyl or (C₂–C₉)heteroaryl groups may optionally be substituted with one, two, or three substituents independently selected from the group consisting of halogen, cyano, and (C₁–C₆)alkyl to form a compound of the formula (IVa2-1)

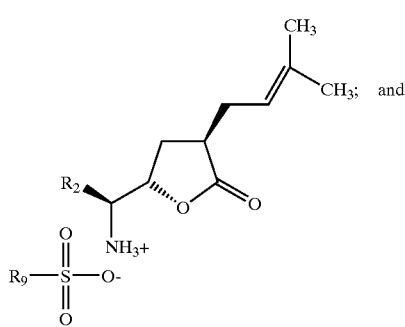

(IVa2-1)

b) coupling the compound (IVa2-1) so formed with a compound having the formula R₁—CO—X, wherein X is hydroxy or halogen.

In yet a sixth aspect, the present invention relates to methods of making compounds of the formula (IIa2-1)

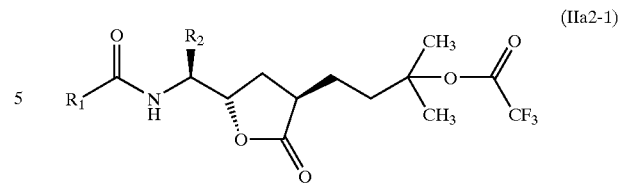

(IIa2-1)

wherein:

R₁ is (C₂–C₉)heteroaryl optionally substituted with one, two or three substituents independently selected from the group consisting of hydrogen, halogen, cyano, (C₁–C₆)alkyl, hydroxy, hydroxy-(C₁–C₆)alkyl, (C₁–C₆)alkoxy, (C₁–C₆)alkoxy(C₁–C₆)alkyl, HO—(C=O)—, (C₁–C₆)alkyl-O—(C=O)—, HO—(C=O)—(C₁–C₆)alkyl, (C₁–C₆)alkyl-O—(C=O)—(C₁–C₆)alkyl, (C₁–C₆)alkyl-(C=O)—O—, (C₁–C₆)alkyl-(C=O)—O—(C₁–C₆)alkyl, H(O=C)—, H(O=C)—(C₁–C₆)alkyl, (C₁–C₆)alkyl(O=C)—, (C₁–C₆)alkyl(O=C)—(C₁–C₆)alkyl, NO₂, amino, (C₁–C₆)alkylamino, [(C₁–C₆)alkyl]₂amino, amino (C₁–C₆)alkyl, (C₁–C₆)alkylamino(C₁–C₆)alkyl, [(C₁–C₆)alkyl]₂amino(C₁–C₆)alkyl, H₂N—(C=O)—, (C₁–C₆)alkyl-NH—(C=O)—, [(C₁–C₆)alkyl]₂N—(C=O)—, H₂N(C=O)—(C₁–C₆)alkyl, (C₁–C₆)alkyl-HN(C=O)—(C₁–C₆)alkyl, [(C₁–C₆)alkyl]₂N—(C=O)—(C₁–C₆)alkyl, H(O=C)—NH—, (C₁–C₆)alkyl(C=O)—NH, (C₁–C₆)alkyl(C=O)—[NH](C₁–C₆)alkyl, (C₁–C₆)alkyl(C=O)—[N(C₁–C₆)alkyl](C₁–C₆)alkyl, (C₁–C₆)alkyl-S—, (C₁–C₆)alkyl-(S=O)—, (C₁–C₆)alkyl-SO₂—, (C₁–C₆)alkyl-SO₂—NH—, H₂N—SO₂—, H₂N—SO₂—(C₁–C₆)alkyl, (C₁–C₆)alkylHN—SO₂—(C₁–₆)alkyl, [(C₁–C₆)alkyl]₂N—SO₂—(C₁–C₆)alkyl, CF₃S₃—, (C₁–C₆)alkyl-SO₃—, phenyl, (C₃–C₁₀)cycloalkyl, (C₂–C₉)heterocycloalkyl, and (C₂–C₉)heteroaryl;

R₂ is phenyl-(CH₂)ₘ—, naphthyl-(CH₂)ₘ—, (C₃–C₁₀)cycloalkyl-(CH₂)ₘ—, (C₁–C₆)alkyl or (C₂–C₉)heteroaryl-(CH₂)ₘ—, wherein each of said phenyl, naphthyl, (C₃–C₁₀)cycloalkyl or (C₂–C₉)heteroaryl moieties of said phenyl-(CH₂)ₘ—, naphthyl-(CH₂)ₘ—, (C₃–C₁₀)cycloalkyl-(CH₂)ₘ— or (C₂–C₉)heteroaryl-(CH₂)ₘ— groups may optionally be substituted with one, two, or three substituents independently selected from the group consisting of hydrogen, halogen, CN, (C₁–C₆)alkyl, hydroxy, hydroxy-(C₁–C₆)alkyl, (C₁–C₆)alkoxy, (C₁–C₆)alkoxy(C₁–C₆)alkyl, HO—(C=O)—, (C₁–C₆)alkyl-O—(C=O)—, HO—(C=O)—(C₁–C₆)alkyl, (C₁–C₆)alkyl-O—(C=O)—(C₁–C₆)alkyl, (C₁–C₆)alkyl-(C=O)—O—, (C₁–C₆)alkyl-(C=O)—O—(C₁–C₆)alkyl, H(O=C)—, H(O=C)—(C₁–C₆)alkyl, (C₁–C₆)alkyl(O=C)—, (C₁–C₆)alkyl(O=C)—(C₁–C₆)alkyl, NO₂, amino, (C₁–C₆)alkylamino, [(C₁–C₆)alkyl]₂ amino, amino(C₁–C₆)alkyl, (C₁–C₆)alkylamino(C₁–C₆)alkyl, [(C₁–C₆)alkyl]₂amino(C₁–C₆)alkyl, H₂N—(C=O)—, (C₁–C₆)alkyl-NH—(C=O)—, [(C₁–C₆)alkyl]₂N—(C=O)—, H₂N(C=O)—(C₁–C₆)alkyl, (C₁–C₆)alkyl-HN(C=O)—(C₁–C₆)alkyl, [(C₁–C₆)alkyl]₂N—(C=O)—(C₁–C₆)alkyl, H(O=C)—NH—, (C₁–C₆)alkyl(C=O)—NH, (C₁–C₆)alkyl(C=O)—[NH](C₁–C₆)alkyl, (C₁–C₆)alkyl(C=O)—[N(C₁–C₆)alkyl](C₁–C₆)alkyl, (C₁–C₆)alkyl-S—, (C₁–C₆)alkyl-(S=O)—, (C₁–C₆)alkyl-SO₂—, (C₁–C₆)alkyl-SO₂—NH—, H₂N—SO₂—, H₂N—SO₂—(C₁–C₆)alkyl, (C₁–C₆)alkylHN—SO₂—(C₁–C₆)alkyl, [(C₁–C₆)alkyl]₂N—SO₂—(C₁–C₆)alkyl, CF₃SO₃—, (C₁–C₆)alkyl-SO₃—, phenyl, phenoxy, benzyloxy, (C₃–C₁₀)cycloalkyl, (C₂–C₉)heterocycloalkyl, and (C₂–C₉)heteroaryl; and m is 0, 1, 2, 3, or 4 wherein the method comprises:

a) reacting and a compound of the formula (IVa1-1)

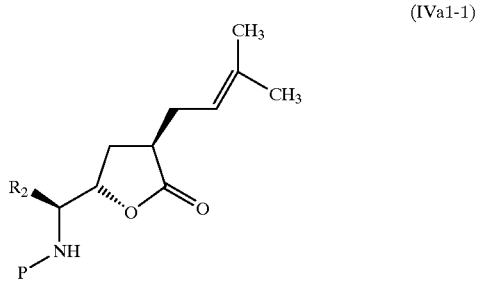

wherein P is a protecting group, with a compound of the formula $R_9$—$SO_2$—OH wherein $R_9$ is and is phenyl, naphthyl, ($C_3$–$C_{10}$)cycloalkyl, ($C_1$–$C_6$)alkyl or ($C_2$–$C_9$)heteroaryl, wherein each of said phenyl, naphthyl, ($C_3$–$C_{10}$)cycloalkyl or ($C_2$–$C_9$)heteroaryl groups may optionally be substituted with one, two, or three substituents independently selected from the group consisting of halogen, cyano, and ($C_1$–$C_6$)alkyl to form a compound of the formula (IVa2-1)

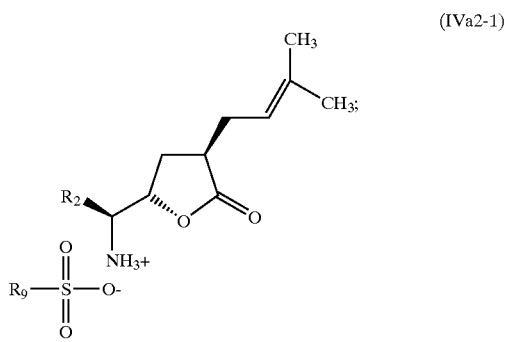

b) coupling the compound (IVa2-1) so formed with a compound having the formula $R_1$—CO—X, wherein X is hydroxy or halogen to form a compound of the formula (IIIa2-1)

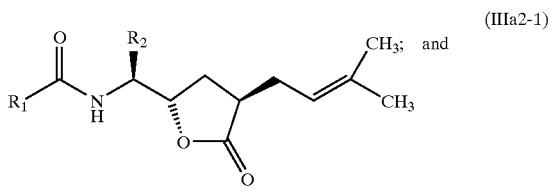

c) reacting the compound (IIIa2-1) so formed with trifluoroacetic acid.

The present invention also relates, in a seventh aspect, to methods of making compounds of the formula (Ia-1)

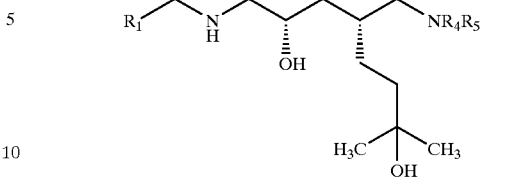

wherein:

$R_1$ is ($C_2$–$C_9$)heteroaryl optionally substituted with one, two or three substituents independently selected from the group consisting of hydrogen, halogen, cyano, ($C_1$–$C_6$)alkyl, hydroxy, hydroxy-($C_1$–$C_6$)alkyl, ($C_1$–$C_6$)alkoxy, ($C_1$–$C_6$)alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, H(O=C)—, H(O=C)—($C_1$–$C_6$)alkyl, ($C_1$–$C_6$)alkyl(O=C)—, ($C_1$–$C_6$)alkyl(O=C)—($C_1$–$C_6$)alkyl, $NO_2$, amino, ($C_1$–$C_6$)alkylamino, [($C_1$–$C_6$)alkyl]$_2$amino, amino ($C_1$–$C_6$)alkyl, ($C_1$–$C_6$)alkylamino($C_1$–$C_6$)alkyl, [($C_1$–$C_6$)alkyl]$_2$amino($C_1$–$C_6$)alkyl, $H_2N$—(C=O)—, ($C_1$–$C_6$)alkyl-NH—(C=O)—, [($C_1$–$C_6$)alkyl]$_2$N—(C=O)—, $H_2N$(C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH ($C_1$–$C_6$)alkyl (C=O)—[NH]($C_1$–$C_6$)alkyl, ($C_1$–$C_6$)alkyl(C=O)—[N ($C_1$–$C_6$)alkyl]($C_1$–$C_6$)alkyl, ($C_1$–$C_6$)alkyl-S—, ($C_1$–$C_6$) alkyl-(S=O)—, ($C_1$–$C_6$)alkyl-$SO_2$—, ($C_1$–$C_6$)alkyl-$SO_2$—NH—, $H_2N$—$SO_2$—, $H_2N$—$SO_2$—($C_1$–$C_6$)alkyl, ($C_1$–$C_6$)alkylHN—$SO_2$—($C_1$–$C_6$)alkyl, [($C_1$–$C_6$)alkyl]$_2$N—$SO_2$—($C_1$–$C_6$)alkyl, $CF_3SO_3$—, ($C_1$–$C_6$)alkyl-$SO_3$—, phenyl ($C_3$–$C_{10}$)cycloalkyl, ($C_2$–$C_9$)heterocycloalkyl, and ($C_2$–$C_9$) heteroaryl;

$R_2$ is phenyl-$(CH_2)_m$—, naphthyl-$(CH_2)_m$—, ($C_3$–$C_{10}$) cycloalkyl-$(CH_2)_m$—, ($C_1$–$C_6$)alkyl or ($C_2$–$C_9$)heteroaryl-$(CH_2)_m$—, wherein each of said phenyl, naphthyl, ($C_3$–$C_{10}$) cycloalkyl or ($C_2$–$C_9$)heteroaryl moieties of said phenyl-$(CH_2)_m$—, naphthyl-$(CH_2)_m$—, ($C_3$–$C_{10}$)cycloalkyl-$(CH_2)_m$— or ($C_2$–$C_9$)heteroaryl-$(CH_2)_m$— groups may optionally be substituted with one, two, or three substituents independently selected from the group consisting of hydrogen, halogen, CN, ($C_1$–$C_6$)alkyl, hydroxy, hydroxy-($C_1$–$C_6$) alkyl, ($C_1$–$C_6$)alkoxy, ($C_1$–$C_6$)alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, H(O=C)—, H(O=C)—($C_1$–$C_6$)alkyl, ($C_1$–$C_6$)alkyl(O=C)—, ($C_1$–$C_6$)alkyl(O=C)—($C_1$–$C_6$) alkyl, $NO_2$, amino, ($C_1$–$C_6$)alkylamino, [($C_1$–$C_6$)alkyl]$_2$ amino, amino($C_1$–$C_6$)alkyl, ($C_1$–$C_6$)alkylamino($C_1$–$C_6$) alkyl, [($C_1$–$C_6$)alkyl]$_2$amino($C_1$–$C_6$)alkyl, $H_2N$—(C=O)—, ($C_1$–$C_6$)alkyl-NH—(C=O)—, [($C_1$–$C_6$)alkyl]$_2$ N—(C=O)—, $H_2N$(C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)—[NH]($C_1$–$C_6$)alkyl, ($C_1$–$C_6$) alkyl(C=O)—[N($C_1$–$C_6$)alkyl]($C_1$–$C_6$)alkyl, ($C_1$–$C_6$) alkyl-S—, ($C_1$–$C_6$)alkyl-(S=O)—, ($C_1$–$C_6$)alkyl-$SO_2$—, ($C_1$–$C_6$)alkyl-$SO_2$—NH—, $H_2N$—$SO_2$—, $H_2N$—$SO_2$—($C_1$–$C_6$)alkyl, ($C_1$–$C_6$)alkylHN—$SO_2$—($C_1$–$C_6$)alkyl, [($C_1$–$C_6$)alkyl]$_2$N—$SO_2$—($C_1$–$C_6$)alkyl, $CF_3SO_3$—, ($C_1$–$C_6$)alkyl-$SO_3$—, phenyl, phenoxy, benzyloxy, ($C_3$–$C_{10}$) cycloalkyl, ($C_2$–$C_9$)heterocycloalkyl, and ($C_2$–$C_9$) heteroaryl;

$R_4$ is hydrogen, $(C_1-C_6)$alkyl, hydroxy, $(C_1-C_6)$alkoxy, hydroxy$(C_1-C_6)$alkyl, $(C_1-C_6)$alkoxy$(C=O)$—, $(C_3-C_{10})$cycloalkyl-$(CH_2)_q$—, $(C_2-C_9)$heterocycloalkyl-$(CH_2)_q$—, $(C_2-C_9)$heteroaryl-$(CH_2)_q$—, phenyl-$(CH_2)_q$—, or naphthyl-$(CH_2)_q$—; wherein said $(C_2-C_9)$heterocycloalkyl, $(C_2-C_9)$heteroaryl, phenyl and naphthyl groups may be optionally substituted with one or two substituents from the group consisting of hydrogen, halogen, cyano, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—$(C=O)$—, $(C_1-C_6)$alkyl-O—$(C=O)$—, HO—$(C=O)$—$(C_1-C_6)$alkyl, $(C_1-C_6)$alkyl-O—$(C=O)$—$(C_1-C_6)$alkyl, $(C_1-C_6)$alkyl-$(C=O)$—O—, $(C_1-C_6)$alkyl-$(C=O)$—O—$(C_1-C_6)$alkyl, H$(O=C)$—, H$(O=C)$—$(C_1-C_6)$alkyl, $(C_1-C_6)$alkyl$(O=C)$—, $(C_1-C_6)$alkyl$(O=C)$—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—$(C=O)$—, $(C_1-C_6)$alkyl-NH—$(C=O)$—, $[(C_1-C_6)$alkyl$]_2N$—$(C=O)$—, $H_2N(C=O)$—$(C_1-C_6)$alkyl, $(C_1-C_6)$alkyl-HN$(C=O)$—$(C_1-C_6)$alkyl, $[(C_1-C_6)$alkyl$]_2N$—$(C=O)$—$(C_1-C_6)$alkyl, H$(O=C)$—NH—, $(C_1-C_6)$alkyl$(C=O)$—NH, $(C_1-C_6)$alkyl$(C=O)$—[NH]$(C_1-C_6)$alkyl, $(C_1-C_6)$alkyl$(C=O)$—[N$(C_1-C_6)$alkyl]$(C_1-C_6)$alkyl, $(C_1-C_6)$alkyl-S—, $(C_1-C_6)$alkyl-$(S=O)$—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$, phenyl, $(C_3-C_{10})$cycloalkyl, $(C_2-C_9)$heterocycloalkyl, and $(C_2-C_9)$heteroaryl;

$R_5$ is hydrogen, $(C_1-C_6)$alkyl or amino; or $R_4$ and $R_5$ together with the nitrogen atom to which they are attached form a $(C_2-C_9)$heterocycloalkyl group optionally substituted with one or two substituents selected from the group consisting of hydrogen, halogen, cyano, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—$(C=O)$—, $(C_1-C_6)$alkyl-O—$(C=O)$—, HO—$(C=O)$—$(C_1-C_6)$alkyl, $(C_1-C_6)$alkyl-O—$(C=O)$—$(C_1-C_6)$alkyl, $(C_1-C_6)$alkyl-$(C=O)$—O—, $(C_1-C_6)$alkyl-$(C=O)$—O—$(C_1-C_6)$alkyl, H$(O=C)$—, H$(O=C)$—$(C_1-C_6)$alkyl, $(C_1-C_6)$alkyl$(O=C)$—, $(C_1-C_6)$alkyl$(O=C)$—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—$(C=O)$—, $(C_1-C_6)$alkyl-NH—$(C=O)$—, $[(C_1-C_6)$alkyl$]_2N$—$(C=O)$—, $H_2N(C=O)$—$(C_1-C_6)$alkyl, $(C_1-C_6)$alkyl-HN$(C=O)$—$(C_1-C_6)$alkyl, $[(C_1-C_6)$alkyl$]_2N$—$(C=O)$—$(C_1-C_6)$alkyl, H$(O=C)$—NH—, $(C_1-C_6)$alkyl$(C=O)$—NH, $(C_1-C_6)$alkyl$(C=O)$—[NH]$(C_1-C_6)$alkyl, $(C_1-C_6)$alkyl$(C=O)$—[N$(C_1-C_6)$alkyl]$(C_1-C_6)$alkyl, $(C_1-C_6)$alkyl-S—, $(C_1-C_6)$alkyl-$(S=O)$—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl;

m is 0, 1, 2, 3, or 4; and q is 0, 1, 2, 3, or 4;

wherein the method comprises:

a) reacting a compound of the formula (IVa1-1)

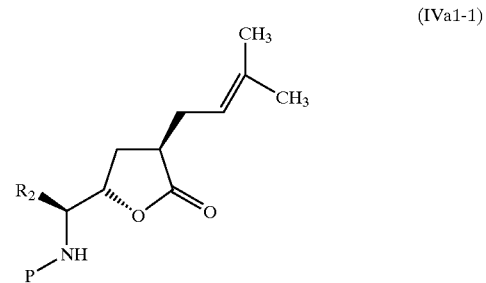

(IVa1-1)

wherein P is a protecting group, with a compound of the formula $R_9$—$SO_2$—OH wherein $R_9$ is and is phenyl, naphthyl, $(C_3-C_{10})$cycloalkyl, $(C_1-C_6)$alkyl or $(C_2-C_9)$heteroaryl, wherein each of said phenyl, naphthyl, $(C_3-C_{10})$cycloalkyl or $(C_2-C_9)$heteroaryl groups may optionally be substituted with one, two, or three substituents independently selected from the group consisting of halogen, cyano, and $(C_1-C_6)$alkyl to form a compound of the formula (IVa2-1)

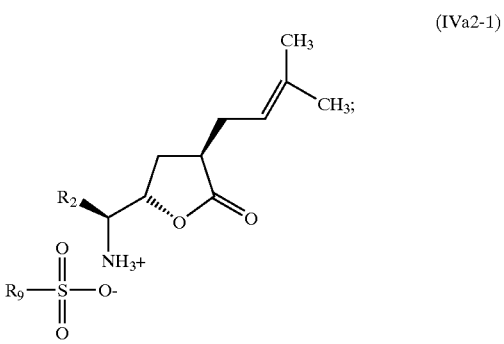

(IVa2-1)

b) coupling the compound (IVa2-1) so formed with a compound having the formula $R_1$—CO—X, wherein X is hydroxy or halogen to form a compound of the formula (IIIa2-1)

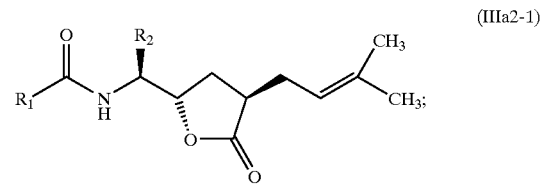

(IIIa2-1)

c) reacting the compound (IIIa2-1) so formed with trifluoroacetic acid to form a compound of the formula (IIa2-1)

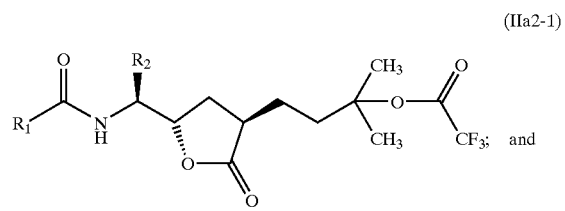

(IIa2-1)

d) reacting the compound of the formula (IIa2-1) so formed with an amine of the formula $NHR_4R_5$.

In one preferred embodiment of any of the aforementioned aspects, the compound of the formula (IVa1-1) is formed by reacting a compound of the formula (V-1)

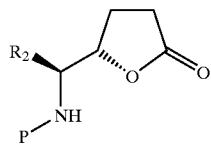

(V-1)

wherein P is a protecting group, with 4-halo-2-methyl-2-butene in the presence of a base.

In an eighth aspect, the present invention relates to methods of deprotecting t-butoxy carbonyl protected compounds, wherein the method comprises reacting the protected compound with phosphoric acid.

In a ninth aspect, the present invention relates to compounds of the formula (IVa2-1):

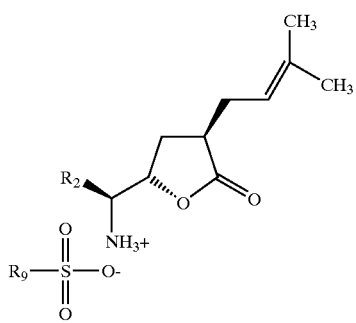

(IVa2-1)

wherein:

$R_2$ is phenyl-$(CH_2)_m$—, naphthyl-$(CH_2)_m$—, $(C_3-C_{10})$cycloalkyl-$(CH_2)_m$—, $(C_1-C_6)$alkyl or $(C_2-C_9)$heteroaryl-$(CH_2)_m$—, wherein each of said phenyl, naphthyl, $(C_3-C_{10})$cycloalkyl or $(C_2-C_9)$heteroaryl moieties of said phenyl-$(CH_2)_m$—, naphthyl-$(CH_2)_m$—, $(C_3-C_{10})$cycloalkyl-$(CH_2)_m$ — or $(C_2-C_9)$heteroaryl-$(CH_2)_m$— groups may optionally be substituted with one, two, or three substituents independently selected from the group consisting of hydrogen, halogen, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl]$_2$ amino, amino $(C_1-C_6)$alkyl, $(C_1-C_6)$alkylamino$(C_1-C_6)$alkyl, $[(C_1-C_6)$alkyl]$_2$amino$(C_1-C_6)$alkyl, $H_2N$—(C=O)—, $(C_1-C_6)$alkyl-NH—(C=O)—, $[(C_1-C_6)$alkyl]$_2$ N—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl]$_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl]$_2$N—$SO_2$—$(C_1-C_6)$alkyl, $CF_3SO_3$—, $(C_1-C_6)$alkyl-$SO_3$—, phenyl, phenoxy, benzyloxy, $(C_3-C_{10})$cycloalkyl, $(C_2-C_9)$heterocycloalkyl, and $(C_2-C_9)$heteroaryl;

$R_9$ is and is phenyl, naphthyl, $(C_3-C_{10})$cycloalkyl, $(C_1-C_6)$alkyl or $(C_2-C_9)$heteroaryl, wherein each of said phenyl, naphthyl, $(C_3-C_{10})$cycloalkyl or $(C_2-C_9)$heteroaryl groups may optionally be substituted with one, two, or three substituents independently selected from the group consisting of halogen, cyano, and $(C_1-C_6)$alkyl; and m is 0, 1, 2, 3, or 4;

and the salts and esters thereof.

The present invention also relates, in an eleventh aspect, to compounds of the formula (IIIa1-1):

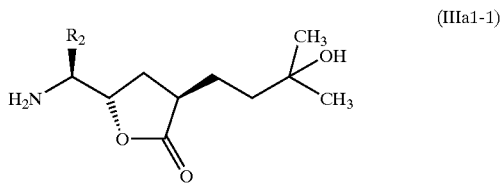

(IIIa1-1)

wherein:

$R_2$ is phenyl-$(CH_2)_m$—, naphthyl-$(CH_2)_m$—, $(C_3-C_{10})$cycloalkyl-$(CH_2)_m$—, $(C_1-C_6)$alkyl or $(C_2-C_9)$heteroaryl-$(CH_2)_m$—, wherein each of said phenyl, naphthyl, $(C_3-C_{10})$cycloalkyl or $(C_2-C_9)$heteroaryl moieties of said phenyl-$(CH_2)_m$—, naphthyl-$(CH_2)_m$—, $(C_3-C_{10})$cycloalkyl-$(CH_2)_m$ — or $(C_2-C_9)$heteroaryl-$(CH_2)_m$— groups may optionally be substituted with one, two, or three substituents independently selected from the group consisting of hydrogen, halogen, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl]$_2$ amino, amino $(C_1-C_6)$alkyl, $(C_1-C_6)$alkylamino$(C_1-C_6)$alkyl, $[(C_1-C_6)$alkyl]$_2$amino$(C_1-C_6)$alkyl, $H_2N$—(C=O)—, $(C_1-C_6)$alkyl-NH—(C=O)—, $[(C_1-C_6)$alkyl]$_2$ N—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl]$_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl]$_2$N—$SO_2$—$(C_1-C_6)$alkyl, $CF_3SO_3$—, $(C_1-C_6)$alkyl-$SO_3$—, phenyl, phenoxy, benzyloxy, $(C_3-C_{10})$cycloalkyl, $(C_2-C_9)$heterocycloalkyl, and $(C_2-C_9)$heteroaryl;

m is 0, 1, 2, 3, or 4;

and the salts and esters thereof.

In preferred embodiments of these aspects of the present invention, $R_2$ is 3-fluorobenzyl, $R_1$ is quinoxaline and/or the compound of formula (Ia-1) is quinoxaline-2-carboxylic acid [4(R)-carbamoyl-1(S)-(3-fluoro-benzyl)-2(S),7-dihydroxy-7-methyl-octyl]-amide.

In further preferred embodiments, the protecting group is carbobenzyloxy, t-butoxy carbonyl, or 9-fluorenyl-methylenoxy carbonyl, preferably is t-butoxy carbonyl.

The present invention further relates, in a twelfth aspect, to compound of the formula IIa1-3

(IIa1-3)

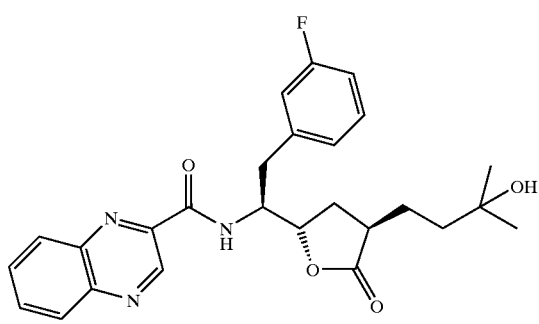

and the salts and esters thereof.

It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of exemplary embodiments of the invention and the examples included therein.

Before the present compounds and methods are disclosed and described, it is to be understood that this invention is not limited to specific synthetic methods of making that may of course vary. It is also to be understood that the terminology used herein is for the purpose of describing particular embodiments only and is not intended to be limiting.

In this specification and in the claims that follow, reference will be made to a number of terms that shall be defined to have the following meanings:

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Such alkyl and alkoxy groups may be substituted with one, two or three halogen and/or hydroxy atoms, preferably fluorine atoms.

Unless otherwise indicated, "halogen" includes fluorine, chlorine, bromine, and iodine.

"$(C_3-C_{10})$cycloalkyl" when used herein refers to cycloalkyl groups containing zero to two levels of unsaturation such as cyclopropyl, cyclobutyl, cyclopentyl, cyclopentenyl, cyclohexyl, cyclohexenyl, 1,3-cyclohexadiene, cycloheptyl, cycloheptenyl, bicyclo[3.2.1]octane, norbornanyl, and the like.

"$(C_2-C_9)$heterocycloalkyl" when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, and the like. One of ordinary skill in the art will understand that the connection of said ($C_2-C_9$)heterocycloalkyl rings is through a carbon or a sp$^3$ hybridized nitrogen heteroatom.

"$(C_2-C_9)$heteroaryl" when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl, and the like. One of ordinary skill in the art will understand that the connection of said ($C_2-C_9$)heterocycloalkyl rings is through a carbon atom or a sp$^3$ hybridized nitrogen heteroatom.

"Aryl" when used herein refers to phenyl or naphthyl.

"Protected amine" and "protected amino" refers to an amine group with one of the hydrogen atoms replaced with a protecting group (P). Any suitable protecting group may be used for amine protection. Suitable protecting groups include carbobenzyloxy, t-butoxy carbonyl (BOC) or 9-fluorenyl-methylenoxy carbonyl.

By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained.

The term "subject" is meant an individual. Preferably, the subject is a mammal such as a primate, and more preferably, a human. Thus, the "subject" can include domesticated animals, livestock, and laboratory animals.

In general, "effective amount" or "effective dose" means the amount needed to achieve the desired result or results (treating or preventing the condition). One of ordinary skill in the art will recognize that the potency and, therefore, an "effective amount" can vary for the various compounds used in the invention. One skilled in the art can readily assess the potency of the compounds.

Unless otherwise noted, numerical values described and claimed herein are approximate. Variation within the values may be attributed to equipment calibration, equipment errors, purity of the materials, among other factors. Additionally, variation may be possible, while still obtaining the same result.

The compounds and processes of the present invention are useful in the manufacture of dihydroxyhexanoic acid derivatives. The present invention includes methods of making a compound of the formula (IVa1-1) as shown in Scheme 1.

Scheme 1

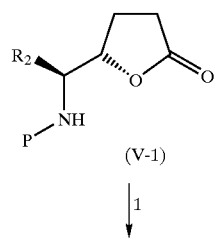

(V-1)

↓1

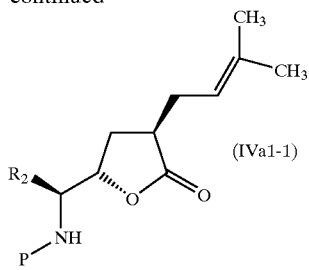

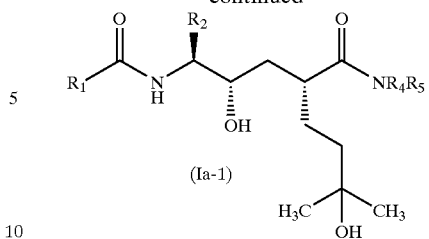

In step 1 of Scheme 1, the compound of the formula (IVa1-1) may be formed by reacting 4-halo-2-methyl-2-butene and a compound of the formula (V-1) in the presence of a base. Exemplary bases include lithium dialkyl amides such as lithium-N-isopropyl-N-cyclohexylamide, lithium bis(trimethylsilyl)amide, lithium di-isopropylamide, and potassium hydride. Suitable solvents include aprotic polar solvents such as ethers (such as tetrahydrofuran, glyme or dioxane), benzene, or toluene, preferably tetrahydrofuran. The aforesaid reaction is conducted at a temperature from about −78° C. to about 0° C., preferably at about −78° C. In one embodiment, alkylation of the lactone (V-1) is accomplished by reacting the lactone (V-1) with lithium bis(trimethylsilyl)amide and dimethylallyl bromide in tetrahydrofuran at a temperature from about −78° C. to about −50° C. Reaction times range from several hours or if an additive such as dimethyl imidazolidinone is present, the reaction may be complete in minutes.

Compounds of formula (IVa1-1) may be used to produce compounds of the formula (Ia-1) according to Scheme 2:

Scheme 2

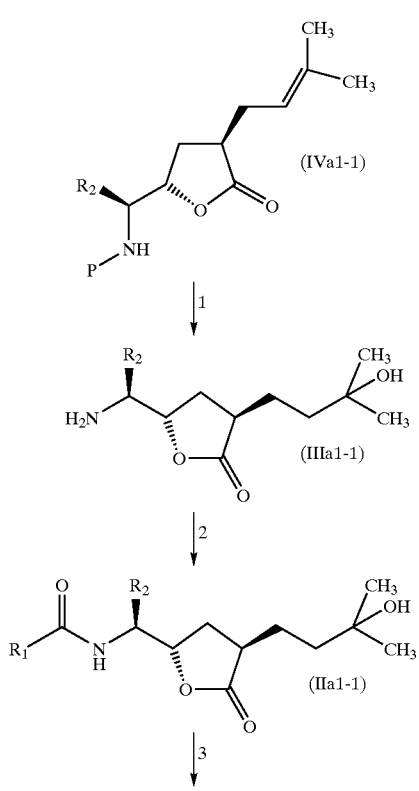

In step 1 of Scheme 2, a compound of the formula (IIIa1-1) is formed by reacting a compound of the formula (IVa1-1) with phosphoric acid. Preferably, this reaction occurs in any suitable solvent, such as non-alcoholic solvents. Two preferred solvents include tetrahydrofuran and dichloromethane. The reaction may take place at any suitable temperature, preferably from about −25° C. to about 120° C., more preferably from about 15° C. to about 40° C. Reaction time is dependent on temperature and batch size, amount other factors, but typically reaction time is from about 2 hours to about 14 hours.

Step 2 of Scheme 2 depicts coupling a compound IIIa1-1 with a compound having the formula $R_1$—CO—X to form a compound having the formula (IIa1-1). This coupling reaction is generally conducted at a temperature from about −30° C. to about 80° C., preferably from about 0° C. to about 25° C. The coupling reaction may occur with a coupling reagent that activates the acid functionality. Exemplary coupling reagents include dicyclohexylcarbodiimide/hydroxybenzotriazole (DCC/HBT), N-3-dimethylaminopropyl-N'-ethylcarbodiimide (EDC/HBT), 2-ethyoxy-1-ethoxycarbonyl-1,2-dihydroquinoline (EEDQ), carbonyl diimidazole (CDI), and diethylphosphorylcyanide. The coupling is conducted in an inert solvent, preferably an aprotic solvent, such as tetrahydrofuran, acetonitrile, dichloromethane, chloroform, or N,N-dimethylformamide. One preferred solvent is tetrahydrofuran. In one embodiment, quinoxaline acid is combined with CDI in anhydrous tetrahydrofuran and heated to provide the acyl imidazole. Compound IIIa1-1 is added to the acyl imidazole at room temperature to form the compound IIa1-1.

Step 3 of Scheme 2 includes reacting the compound of formula IIa1-1 with an amine having a formula $NHR_4R_5$ to form a compound of the formula (Ia-1). In one embodiment, the amine is ammonia either anhydrous in an organic solvent or as an aqueous solution of ammonium hydroxide added to a polar solvent at a temperature from about −10° C. to about 35° C., preferably at about 30° C. Suitable solvents include, alcohols, such as methanol, ethanol, or butanols; ethers such as tetrahydrofuran, glyme or dioxane; or a mixture thereof, including aqueous mixtures. Preferably the solvent is methanol. In one embodiment, the compound IIa1-1 is dissolved in methanol which has been saturated with ammonia gas. In another embodiment, the compound IIa1-1 in methanol is treated with ammonium hydroxide in tetrahydrofuran at room temperature.

Scheme 3 represents an alternative method to form compounds of formula Ia-1 from compounds of formula IVa1-1.

Scheme 3

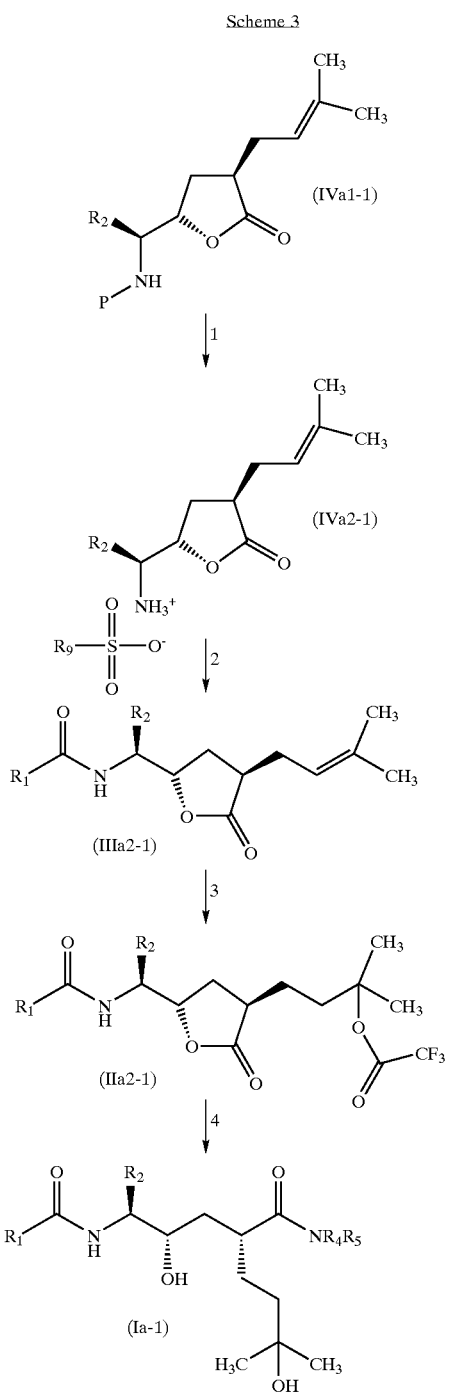

In step 1 of Scheme 3, a compound of the formula (IVa1-1) is reacted with a compound of the formula $R_9$—$SO_2$—OH to form a compound of the formula (IVa2-1). Any suitable acidic deprotection reaction may be performed. In one example, an excess of p-toluenesulfonic acid hydrate in ethyl acetate is introduced to the compound IVa1-1 at room temperature. Suitable solvents include ethyl acetate, alcohols, tetrahydrofuran, and mixtures thereof. The reaction may proceed at ambient or elevated temperatures. Typically, the reaction is substantially complete within two and twelve hours. The resulting compound IVa2-1 may be crystallized and separated from the reaction mixture, and may be further purified to remove impurities by recrystallization from hot ethyl acetate.

In step 2 of Scheme 3, the compound IVa2-1 may be coupled with a compound having the formula $R_1$—CO—X to form a compound of the formula (IIIa2-1). This coupling reaction is generally conducted at a temperature from about −30° C. to about 80° C., preferably from about 0° C. to about 25° C. The coupling reaction may occur with a coupling reagent that activates the acid functionality. Exemplary coupling reagents include dicyclohexylcarbodiimide/ hydroxybenzotriazole. (DCC/HBT), N-3-dimethylaminopropyl-N'-ethylcarbodiimide (EDC/HBT), 2-ethyoxy-1-ethoxycarbonyl-1,2-dihydroquinoline (EEDQ), carbonyl diimidazole (CDI)/ dimethylaminopyridine (DMAP), and diethylphosphorylcyanide. The coupling is conducted in an inert solvent, preferably an aprotic solvent, such as acetonitrile, dichloromethane, chloroform, or N,N-dimethylformamide. One preferred solvent is methylene chloride. In one embodiment, quinoxaline acid is combined with methylene chloride, oxalyl chloride and a catalytic amount of N,N-dimethylformamide to form an acid chloride complex. The compound IVa2-1 is added to the acid chloride complex followed by triethylamine at a temperature from about 0° C. to about 25° C. to form the compound IIIa2-1.

Step 3 of Scheme 3 includes reacting a compound IIIa2-1 with trifluoroacetic acid to produce a compound of the formula (IIa2-1). In one embodiment, the hydration with trifluoroacetic acid occurs in methylene chloride solution at room temperature. The hydration may take several hours to complete at room temperature. A catalytic amount of sulfuric acid can be added to the reaction solution to increase the rate of reaction.

Step 4 of Scheme 3 includes reacting the compound of formula IIa2-1 with an amine having a formula $NHR_4R_5$ to form a compound of the formula (Ia-1). In one embodiment, the amine is ammonia either anhydrous in an organic solvent or as an aqueous solution of ammonium hydroxide added to a polar solvent at a temperature from about −10° C. to about 35° C., preferably at about 30° C. Suitable solvents include, alcohols, such as methanol, ethanol, or butanols; ethers such as tetrahydrofuran, glyme or dioxane; or a mixture thereof, including aqueous mixtures. Preferably the solvent is methanol. In one embodiment, the compound IIa2-1 is dissolved in methanol which has been saturated with ammonia gas. In another embodiment, the compound IIa2-1 in methanol is treated with ammonium hydroxide in tetrahydrofuran at room temperature.

Moreover, the present invention relates to removing a t-butoxy carbonyl protecting group (BOC or Boc) from a protected compound wherein the method comprises reacting the protected compound with phosphoric acid. Phosphoric acid is a much weaker acid ($pKa_1$ 2.15) than trifluoro-acetic acid (pKa 0.3), methanesulfonic acid (pKa −0.6), Toluene-4-sulfonic acid (pKa −1.3) and other mineral acids.

Phosphoric acid Boc deprotection is especially suitable for substrates with acid sensitive functionalities other than the BOC group. For instance, phosphoric acid is more suitable for optically active compounds with chiral centers next to a carbonyl because of potential epimerization. Moreover, this method also works effectively for deprotection of BOC groups on nitrogen groups such as primary and secondary amines, as well as imidazole nitrogens.

Unless indicated otherwise, the pressure of each of the above reactions is not critical. Generally, the reactions will be conducted at a pressure of about one to about three atmospheres, preferably at ambient pressure (about one atmosphere).

The compounds of the formula IVa2-1 and IIIa1-1are capable of forming a wide variety of different salts with various inorganic and organic acids. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

The compound of the formula Ia-1 and its pharmaceutically acceptable salts (hereinafter also referred to, collectively, as "the active compounds") are potent antagonists of the CCR1 receptors. The active compounds are useful in the treatment or prevention of autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult respiratory distress syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), transplantation tissue rejection, atherosclerosis, restenosis, HIV infectivity (co-receptor usage), and granulomatous diseases (including sarcoidosis, leprosy and tuberculosis).

The activity of the compounds of the formula Ia-1 can be assessed according to procedures known to those of ordinary skill in the art. Examples of recognized methods for determining CCR1 induced migration can be found in Coligan, J. E., Kruisbeek, A. M., Margulies, D. H., Shevach, E. M., Strober, W. editors: *Current Protocols In Immunology*, 6.12.1–6.12.3. (John Wiley and Sons, NY, 1991). One specific example of how to determine the activity of a compound for inhibiting migration is described in detail below.

Chemotaxis Assay

The ability of compounds to inhibit the chemotaxis to various chemokines can be evaluated using standard 48 or 96 well Boyden Chambers with a 5 micron polycarbonate filter. All reagents and cells can be prepared in standard RPMI (BioWhitikker Inc.) tissue culture medium supplemented with 1 mg/ml of bovine serum albumin. Briefly, MIP-1α (Peprotech, Inc., P.O. Box 275, Rocky Hill, N.J.) or other test agonists, were placed into the lower chambers of the Boyden chamber. A polycarbonate filter was then applied and the upper chamber fastened. The amount of agonist chosen is that determined to give the maximal amount of chemotaxis in this system (e.g., 1 nM for MIP-1α should be adequate).

THP-1 cells (ATCC TIB-202), primary human monocytes, or primary lymphocytes, isolated by standard techniques can then be added to the upper chambers in triplicate together with various concentrations of the test compound. Compound dilutions can be prepared using standard serological techniques, and are mixed with cells prior to adding to the chamber.

After a suitable incubation period at 37 degrees centigrade (e.g. 3.5 hours for THP-1 cells, 90 minutes for primary monocytes), the chamber is removed, the cells in the upper chamber aspirated, the upper part of the filter wiped and the number of cells migrating can be determined according to the following method.

For THP-1 cells, the chamber (a 96 well variety manufactured by Neuroprobe) can be centrifuged to push cells off the lower chamber and the number of cells can be quantitated against a standard curve by a color change of the dye fluorocein diacetate.

For primary human monocytes, or lymphocytes, the filter can be stained with Dif Quik® dye (American Scientific Products) and the number of cells migrating can be determined microscopically.

The number of cells migrating in the presence of the compound are divided by the number of cells migrating in control wells (without the compound). The quotient is the % inhibition for the compound which can then be plotted using standard graphics techniques against the concentration of compound used. The 50% inhibition point is then determined using a line fit analysis for all concentrations tested. The line fit for all data points must have a coefficient of correlation (R squared) of >90% to be considered a valid assay.

The compounds of formula Ia-1 had $IC_{50}$ values of less than 25 µM, in the Chemotaxis assay.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation. The active compounds of the invention may also be formulated for sustained delivery. Formulations of dihydroxyhexanoic acid derivatives are exemplified in co-pending U.S. patent application Ser. Nos. 60/300,255; 60/300,261; 60/300,256; and 60/300,260, all of which were filed on Jun. 22, 2001 and all of which are incorporated herein in their entireties for all purposes.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g. lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., rheumatoid arthritis) is 0.1 to 1000 mg of the active ingredient per unit dose which could be administered, for example, 1 to 4 times per day.

Aerosol formulations for treatment of the conditions referred to above (e.g., rheumatoid arthritis) in the average adult human are preferably arranged so that each metered dose or "puff" of aerosol contains 20 $\mu$g to 1000 $\mu$g of the compound of the invention. The overall daily dose with an aerosol will be within the range 0.1 mg to 1000 mg. Administration may be several times daily, for example 2, 3, 4 or 8 times, giving for example, 1, 2 or 3 doses each time.

The active agents can be formulated for sustained delivery according to methods well known to those of ordinary skill in the art. Examples of such formulations can be found in U.S. Pat. Nos. 3,538,214, 4,060,598, 4,173,626, 3,119,742, and 3,492,397.

The compounds of the invention can also be utilized in combination therapy with other therapeutic agents such as with immunosuppressant agents such as cyclosporin A and FK-506, Cellcept®, rapamycin, leuflonamide or with classical anti-inflammatory agents (e.g. cyclooxygenase/lipoxegenase inhibitors) such as tenidap, aspirin, acetaminophen, naproxen and piroxicam, steroids including prednisone, azathioprine and biological agents such as OKT-3, anti IL-2 monoclonal antibodies (such as TAC).

Experimental

The following examples are put forth so as to provide those of ordinary skill in the art with a complete disclosure and description of how the compounds, compositions, and methods claimed herein are made and evaluated, and are intended to be purely exemplary of the invention and are not intended to limit the scope of what the inventors regard as their invention. Unless indicated otherwise, percent is percent by weight given the component and the total weight of the composition, temperature is in ° C. or is at ambient temperature, and pressure is at or near atmospheric. Commercial reagents were utilized without further purification. The following abbreviations are herein used:

AA is amino acid
AcOH is acetic acid
BOC is t-butoxy carbonyl
$CDCl_3$ is deuteriotrichloromethane
DMF is N,N-dimethylformamide
EtOAc is ethyl acetate
HCl is hydrochloric acid
IPE is isopropyl ether
LiHMDS is lithium hexamethyidisilazane
MeOH is methanol
THF is tetrahydrofuran
g is grams
L is liter
M is molar
ml is milliliter
mmol is millimole
MHz is mega hertz
N is normal
psi is pounds per square inch
h is hours
min is minutes
sec is seconds
mp is melting point
RT is room temperature
Vacuo is in vacuum
~is roughly approximate to*
HPLC is high pressure liquid chromatography
LCMS is liquid chromatograph mass spectrometer
NMR is nuclear magnetic resonance
TLC is thin layer chromatography Note that all numbers provided herein are approximate, but effort have been made to ensure accuracy with respect to numbers (e.g., amounts, temperature, etc.); however some errors and deviations should be accounted for.

EXAMPLE 1

{2-(3-Fluoro-phenyl)-1-[4-(3-methyl-but-2-enyl)-5-oxo-tetrahydro-furan-2-yl]-ethyl}-carbamic acid tert-butyl ester (IVa1-3)

A 3-neck round bottom flask was dried and purged with nitrogen for 1 h before use. Under nitrogen atmosphere, 1.0 M LiHMDS solution in THF (2.10 eq., 64.9 ml, 57.82 g) was charged to the reaction flask, and it was subsequently cooled to −78° C. [2-(3-Fluoro-phenyl)-1-(5-oxo-tetrahydro-furan-2-yl)-ethyl]-carbamic acid tert-butyl ester (V-3) (10 g, 30.9 mmol) in 50 ml of anhydrous THF was added to the LiHMDS solution dropwise while keeping the reaction temperature below −65° C. After the addition, the reaction was stirred for 30 min at −65° C. to −78° C.

In a separate flask, dimethyl allyl bromide (1.2 eq., 37.1 mmol, 5.53 g, 96% pure by GC) and Dimethyl imidazolidinone (1.2 eq., 37.1 mmol, 4.23 g) in 50 ml of anhydrous THF was pre-cooled to −78° C. The enolate solution was added slowly via a cannula to the bromide solution at −78° C. while maintaining the reaction temperature below −70° C. After the addition, the reaction was stirred for 2 min, and determined completed by HPLC assay of an aliquot.

Acetic acid (4 eq., 28.4 ml) in methyl t-butyl ether (50 ml) was added gradually. The mixture was allowed to warm up slowly to room temperature, and water (100 ml) was added. Layers were separated, and the organic layer was washed with 10% sodium carbonate (100 ml) once, then water (2 times 100 ml). Note: first two washes layer separations were fast, but the last one was slow, and 20 ml of sat. brine solution was added. The organic solution was then concentrated to an oil. (may be slightly water wet, but ok for the next step). 14.1 g crude oil. NMR spectra: $^1$H NMR (CDCl$_3$, 400 MHz) δ 1.34 (s, 9H), 1.56 (s, 3H), 1.64 (s, 3H), 1.87–1.94 (m, 1H), 2.20–2.26 (m, 1H), 2.36–2.42 (m, 1H), 2.63–2.71 (m, 1H), 2.82–2.88 (m, 2H), 3.96 (dt, 2H, J=8.4, 8.4 Hz), 4.41 (t, 1H, J=6.4 Hz), 4.72 (d, 1H, J=9.6 Hz), 4.99–5.00 (m, 1H), 6.87–7.00 (m, 3H), 7.20–7.26 (m, 1H); $^{13}$C NMR (CDCl$_3$, 400 MHz) δ 17.78, 25.68, 28.08, 29.27, 29.33, 38.73, 38.92, 54.32, 78.41, 79.91, 113.43, 113.64, 115.98, 116.18, 119.42, 124.86, 124.88, 129.92, 130.00, 135.21, 139.70, 139.78, 155.79, 161.53, 163.98, 179.38.

EXAMPLE 2

Preparation of 5-[1-Amino-2-(3-fluoro-phenyl)-ethyl]-3-(3-hydroxy-3-methyl-butyl)-dihydro-furan-2-one (IIIa1-2)

The crude oil containing the compound (IVa1-3) (13.2 g, crude) was stirred with 20 ml of methylene chloride and 50 ml of 85% phosphoric acid with good agitation.[1] After 7 h, sample showed reaction completion. The mixture was cooled to 0° C. after diluting with water (50 ml), and 20% sodium hydroxide was added until pH was in the range of 7 to 8.5. Ethyl acetate was added (150 ml), and the layers were separated. The organic solution was dried over magnesium sulfate, and stripped to an oil under vacuum. 9.7 g (crude oil) obtained. This material was not purified, and directly used in the next step.

[1] After the completion of this sequence, it was also demonstrated 1 ml of methylene chloride and 2 ml of 85% phosphoric acid could drive the reaction to completion on a 1 g crude oil scale.

$^1$H NMR (CDCl$_3$, 400 MHz) δ 7.20–7.36 (m, 1H), 6.85–7.01 (m, 3H), 4.36–4.44 (m, 1H), 2.58–3.05 (m, 4H), 2.25–2.40 (m, 1H), 1.80–2.04 (m, 2H), 1.37–1.64 (m, 6H), 1.21 (s, 3H), 1.22 (s, 3H); $^{13}$C NMR (CDCl$_3$, 400 MHz) δ 179.6, 164.1, 161.8, 140.6, 130.2, 130.1, 124.9, 124.8, 116.1, 115.9, 113.7, 113.5, 80.9, 70.5, 56.4, 40.8, 39.8, 30.8, 29.5, 29.0, 26.2, 14.1.

EXAMPLE 3

Preparation of quinoxaline-2-carboxylic acid {2-(3-fluoro-phenyl)-1-[4-(3-hydroxy-3-methyl-butyl)-5-oxo-tetrahydro-furan-2-yl]-ethyl}-amide (IIa1-3)

2-Quinoxaline acid (3.05 g, 1.2 eq) and carbonyl diimidazole (2.72 g, 1.15 eq) were heated in anhydrous THF (30 ml) under nitrogen for 2 h. An aliquot was taken and derivatized quickly with pyrrolidine in acetonitrile (HPLC assay should show complete anhydride formation, on scale, 2-quinoxaline acid will be refluxed in THF first, and atmospherically strip off some THF to ensure complete dryness). The mixture was then cooled, and added via a cannula to the amine (IIIa1-2) (4.5 g, crude oil from example 2) solution [note: no exotherm observed]. The reaction was stirred for 1 h at room temperature, and assay showed no starting material left. The reaction was quenched with water (50 ml). The layers were separated, and the organic phase was washed with 10% NaHCO$_3$ (50 ml) once, and concentrated to give an oil under vacuum.

The oil was water wet, but directly used in the next step. 9.58 (s, 1H), 8.05–8.18 (m, 3H), 7.85–7.88 (m, 2H), 7.81–7.27 (m, 3H), 4.58–4.65 (m, 1H), 3.02–3.20 (m, 1H), 2.44–2.61 (m, 1H), 2.34–2.38 (m, 1H), 1.95–2.08 (m, 1H), 1.76–1.98 (m, 1H), 1.38–1.61 (m, 6H), 1.15 (s, 6H).

EXAMPLE 4

Preparation of quinoxaline-2-carboxylic acid [4(R)-carbamoyl-1(S)-(3-fluoro-benzyl)-2(S),7-dihydroxy-7-methyl-octyl]-amide (Ia-3)

The oil containing the compound IIa1–3 (from example 3) was dissolved in 50 ml of MeOH, and 25 ml of concentrated aqueous ammonia was added. The resulting mixture was stirred at room temperature for 24 h. HPLC assay showed ~3% hydrated lactone remained. The mixture was stripped to approx. 50 ml under reduced pressure (a scrubber is needed on scale). 1 N HCl was added to adjust pH to 2 to 5 range. Methylene chloride was added (150 ml), layers were separated, the methylene chloride layer was washed with 5% sodium carbonate solution (containing 5% sodium chloride). The product was dried over magnesium sulfate, and concentrated to 30 ml. Stirring at 0° C. gave a very thick slurry of recrystallization mixture (but should be stirrable on scale, if necessary 20 ml cold methylene chloride may be added to increase fluidity). The product was isolated by filtration, rinsed with cold methylene chloride and pulled dry. $^1$H and $^{13}$C NMR spectra were identical to that was reported in WO99/40061.

EXAMPLE 5

5-[1-Amino-2-(3-fluoro-phenyl)-ethyl]-3-(3-methyl-2-butenyl)-dihydro-furan-2-one-tosic salt (IVa2-3)

{2-(3-Fluoro-phenyl)-1-[4-(3-methyl-but-2-enyl)-5-oxo-tetrahydro-furan-2-yl]-ethyl}-carbamic acid tert-butyl ester (IVa1-3) (57.36 g, 0.1467 mol) was dissolved in ethyl acetate (180 ml) and p-toluenesulfonic acid hydrate (27.87 g, 0.1467 mol) was added. The reaction was stirred at room temperature overnight. The thick slurry that resulted was diluted with ethyl acetate (220 ml) and hexanes (100 ml). The slurry was stirred for one hour and the solids were collected. The solids (40.6 g) were recrystallized from hot ethyl acetate (350 ml). The solids were collected by filtration, washed with ethyl acetate/hexanes (1:1) and dried in vacuo to provide the desired salt as a white solid, 34.6 g, 51% yield.

EXAMPLE 6

Quinoxaline-2-carboxylic acid {2-(3-fluoro-phenyl)-1-[4-(3-methyl-2-butenyl)-5-oxo-tetrahydro-furan-2-yl]-ethyl}-amide (IIIa2-3)

The tosic salt (IVa2-3) (30 g, 0.0647) from example 5 was dissolved in methylene chloride (300 ml). The solution was cooled to −4° C. and quinoxaline 2-carbonyl chloride (12.47 g, 0.06479) was added as a solid. Triethylamine (18 ml, 0.1296 mol) was added dropwise over four minutes, which caused a mild exotherm to 6° C. The reaction was allowed to warm to room temperature and stirred for one hour. The solution was washed with water, aqueous citric acid, aqueous sodium bicarbonate and brine. The methylene chloride layer was dried over sodium sulfate and evaporated to a thick oil. The only impurity was a small amount of bis-alkylated material.

EXAMPLE 7

Quinoxaline-2-carboxylic acid {2-(3-fluoro-phenyl)-1-[4-(3-methyl-2-trifluoroacetoxy-butyl)-5-oxo-tetrahydro-furan-2-yl]-ethyl}-amide (IIa2-3)

The olefinic lactone (IIIa2-3) (28.96 g, 65 mmol) was dissolved in methylene chloride (35 ml). The solution was cooled to 0° C. and trifluoroacetic acid (44.9 ml, 583 mmol) was added in a slow stream and the cooling was removed. The reaction was stirred for 36 hours at which time it was determined that most of the olefin had reacted. The reaction mixture was diluted with methylene chloride (275 ml) and the solution was added to cold water (200 ml at 0° C.). The layers were separated and the organic were washed with water (300 ml). The organic layer was separated and stirred with free water (200 ml) while the pH was adjusted with solid sodium bicarbonate to greater than pH 7. The methylene chloride layer was separated and evaporated to provide the desired trifluoroacetate as oil, 34.44 g, 95% yield. The spectral data were consistent with the structure and the material was carried on without further purification to the final step.

EXAMPLE 8

Quinoxaline-2-carboxylic acid [4(R)-carbamoyl-1 (S)-(3-fluoro-benzyl)-2(S),7-dihydroxy-7-methyl-octyl]-amide (Ia-3)

A portion of the trifluoroacetate (10 g) from example 7, (IIa2-3) was suspended in methanol (40 ml) and cooled in an ice bath to about 16° C. 28% Aqueous ammonium hydroxide solution (30 ml) was added dropwise over 6 minutes with a rise in temperature to about 20° C. The cooling bath was removed and the reaction mixture was allowed to stir at room temperature overnight during which time a solution formed. The solution was extracted twice with methylene chloride. The combined organics were washed one time with brine, dried over magnesium sulfate and evaporated to a white foam. This material was stirred with fresh methylene chloride (85 ml). A solution was seen initially and followed by precipitation of solids. After two hours, the solids were collected by filtration and washed with methylene chloride and isopropyl ether. After drying in vacuo the yield of desired amide was 5.63 g, 66%. The material was identical to that produced by the other variations of the process.

EXAMPLE 9

Deprotection of Groups with Phosphoric Acid

To a solution of 2-tert-Butoxycarbonylamino-succinic acid 1-benzyl ester (1.0 g, 2.73 mmol) in tetrahydrofuran (1 ml) at room temperature (entry 2, Table A), was added 85% phosphoric acid (2.81 mL, 41 mmol, 15 eq.) dropwise. The mixture was stirred for 4 h, and HPLC assay showed reaction completion. 5 ml of water was added, and the mixture was cooled to 0° C. 50% NaOH solution was added slowly to adjust to pH 7 to 8. The mixture was then extracted with ethyl acetate (2 times 20 ml). The combined ethyl acetate phase was dried over magnesium sulfate, concentrated in vacuo to give the desired product as a white solid (0.57 g, 94%). The product (shown in table A) showed 98.7% purity by HPLC area. It co-eluted with an authentic sample by HPLC, and matched the desired NMR spectral profiles.

All starting materials and reagents were purchased from commercial sources and were used without further purification. $^1$H and $^{13}$C NMR spectra were obtained in DMSO-d$^6$ with DMSO-d$^6$ ($^1$H, 2.49 ppm, $^{13}$C, 39.5 ppm) as an internal reference using a Varian 400. HPLC analyses were carried out using a SB-CN column (4.6 mm×250 mm) with acetonitrile: 0.2% perchloric acid aqueous buffer (20/80 or 40/60) as mobile phase (2 mL/min) and detection at 210 nm wavelength.

The process was repeated for all of the substrates in Table A.

TABLE A

Phosphoric Acid Used as de-BOC Reagent

| Entry | Substrate | Product |
|---|---|---|
| 1 | 2-tert-Butoxycarbonylamino-3-phenyl-propionic acid methyl ester | 2-Amino-3-phenyl-propionic acid methyl ester |
| 2 | 2-tert-Butoxycarbonylamino-succinic acid 1-benzyl ester- | 2-Amino-succinic acid 1-benzyl ester |
| 3 | 4-[2-Carboxy-2-(9H-fluoren-9-ylmethoxycarbonylamino)-ethyl]-imidazole-1-carboxylic acid tert-butyl ester | 2-(9H-Fluoren-9-ylmethoxycarbonylamino)-3-(1H-imidazol-4-yl)-propionic acid |
| 4 | 5-Benzyloxycarbonylamino-2-tert-butoxycarbonylamino-pentanoic acid | 2-Amino-5-benzyloxycarbonylamino-pentanoic acid |
| 5 | 2-tert-Butoxycarbonylamino-3-methyl-butyric acid methyl ester | 2-Amino-3-methyl-butyric acid methyl ester |

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of making a compound of the formula (IIIa1-1)

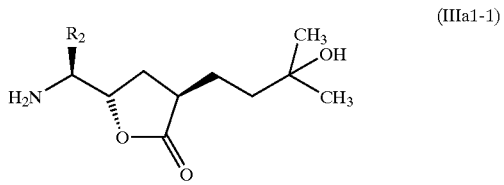

wherein:

R$_2$ is phenyl-(CH$_2$)$_m$—, naphthyl-(CH$_2$)$_m$—, (C$_3$–C$_{10}$)cycloalkyl-(CH$_2$)$_m$—, (C$_1$–C$_6$)alkyl or (C$_2$–C$_9$)heteroaryl-(CH$_2$)$_m$—, wherein each of said phenyl, naphthyl, (C$_3$–C$_{10}$)cycloalkyl or (C$_2$–C$_9$)heteroaryl moieties of said phenyl-(CH$_2$)$_m$—, naphthyl-(CH$_2$)$_m$—, (C$_3$–C$_{10}$)cycloalkyl-(CH$_2$)$_m$— or (C$_2$–C$_9$)heteroaryl-(CH$_2$)$_m$— groups may optionally be substituted with one, two, or three substituents independently selected from the group consisting of hydrogen, halogen, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, NO$_2$, amino, $(C_1-C_6)$alkylamino, [$(C_1-C_6)$alkyl]$_2$amino, amino$(C_1-C_6)$alkyl, $(C_1-C_6)$alkylamino$(C_1-C_6)$alkyl, [$(C_1-C_6)$alkyl]$_2$amino$(C_1-C_6)$alkyl, H$_2$N—(C=O)—, $(C_1-C_6)$alkyl-NH—(C=O)—, [$(C_1-C_6)$alkyl]$_2$N—(C=O)—, H$_2$N(C=O)—$(C_1-C_6)$alkyl, $(C_1-C_6)$alkyl-HN(C=O)—$(C_1-C_6)$alkyl, [$(C_1-C_6)$alkyl]$_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, H$_2$N—SO$_2$—, H$_2$N—SO$_2$-$(C_1-C_6)$alkyl, $(C_1-C_6)$alkylHN—SO$_2$-$(C_1-C_6)$alkyl, [$(C_1-C_6)$alkyl]$_2$N—SO$_2$—$(C_1-C_6)$alkyl, CF$_3$SO$_3$—, $(C_1-C_6)$alkyl-SO$_3$—, phenyl, phenoxy, benzyloxy, $(C_3-C_{10})$cycloalkyl, $(C_2-C_9)$heterocycloalkyl, and $(C_2-C_9)$heteroaryl; and m is 0, 1, 2, 3, or 4 wherein the method comprises reacting a compound of the formula (IVa1-1)

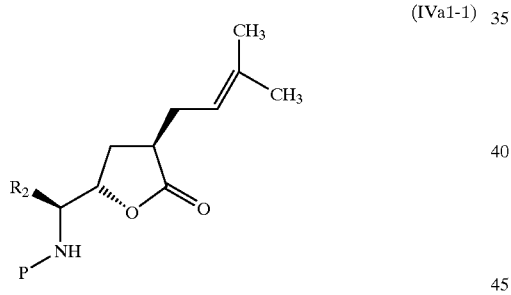

(IVa1-1)

wherein P is a protecting group, with phosphoric acid.

2. A method of making a compound of the formula (IIa1-1)

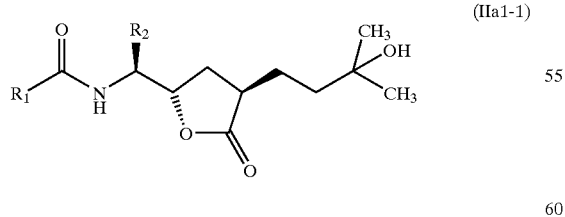

(IIa1-1)

wherein

R$_1$ is $(C_2-C_9)$heteroaryl optionally substituted with one, two or three substituents independently selected from the group consisting of hydrogen, halogen, cyano, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, NO$_2$, amino, $(C_1-C_6)$alkylamino, [$(C_1-C_6)$alkyl]$_2$amino, amino$(C_1-C_6)$alkyl, $(C_1-C_6)$alkylamino$(C_1-C_6)$alkyl, [$(C_1-C_6)$alkyl]$_2$amino$(C_1-C_6)$alkyl, H$_2$N—(C=O)—, $(C_1-C_6)$alkyl-NH—(C=O)—, [$(C_1-C_6)$alkyl]$_2$N—(C=O)—, H$_2$N(C=O)—$(C_1-C_6)$alkyl, $(C_1-C_6)$alkyl-HN(C=O)—$(C_1-C_6)$alkyl, [$(C_1-C_6)$alkyl]$_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, H$_2$N—SO$_2$—, H$_2$N—SO$_2$—$(C_1-C_6)$alkyl, $(C_1-C_6)$alkylHN—SO$_2$—$(C_1-C_6)$alkyl, [$(C_1-C_6)$alkyl]$_2$N—SO$_2$—$(C_1-C_6)$alkyl, CF$_3$SO$_3$—, $(C_1-C_6)$alkyl-SO$_3$—, phenyl, phenoxy, benzyloxy, $(C_3-C_{10})$cycloalkyl, $(C_2-C_9)$heterocycloalkyl, and $(C_2-C_9)$heteroaryl;

R$_2$ is phenyl-(CH$_2$)$_m$—, naphthyl-(CH$_2$)$_m$—, $(C_3-C_{10})$cycloalkyl-(CH$_2$)$_m$—, $(C_1-C_6)$alkyl or $(C_2-C_9)$heteroaryl-(CH$_2$)$_m$—, wherein each of said phenyl, naphthyl, $(C_3-C_{10})$cycloalkyl or $(C_2-C_9)$heteroaryl moieties of said phenyl-(CH$_2$)$_m$—, naphthyl-(CH$_2$)$_m$—, $(C_3-C_{10})$cycloalkyl-(CH$_2$)$_m$— or $(C_2-C_9)$heteroaryl-(CH$_2$)$_m$— groups may optionally be substituted with one, two, or three substituents independently selected from the group consisting of hydrogen, halogen, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, NO$_2$, amino, $(C_1-C_6)$alkylamino, [$(C_1-C_6)$alkyl]$_2$amino, amino$(C_1-C_6)$alkyl, $(C_1-C_6)$alkylamino$(C_1-C_6)$alkyl, [$(C_1-C_6)$alkyl]$_2$amino$(C_1-C_6)$alkyl, H$_2$N—(C=O)—, $(C_1-C_6)$alkyl-NH—(C=O)—, [$(C_1-C_6)$alkyl]$_2$N—(C=O)—, H$_2$N(C=O)—$(C_1-C_6)$alkyl, $(C_1-C_6)$alkyl-HN(C=O)—$(C_1-C_6)$alkyl, [$(C_1-C_6)$alkyl]$_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, H$_2$N—SO$_2$—, H$_2$N—SO$_2$—$(C_1-C_6)$alkyl, $(C_1-C_6)$alkylHN—SO$_2$—$(C_1-C_6)$alkyl, [$(C_1-C_6)$alkyl]$_2$N—SO$_2$—$(C_1-C_6)$alkyl, CF$_3$SO$_3$—, $(C_1-C_6)$alkyl-SO$_3$—, phenyl, phenoxy, benzyloxy, $(C_3-C_{10})$cycloalkyl, $(C_2-C_9)$heterocycloalkyl, and $(C_2-C_9)$heteroaryl; and m is 0, 1, 2, 3, or 4 wherein the method comprises:

a) reacting a compound of the formula (IVa1-1)

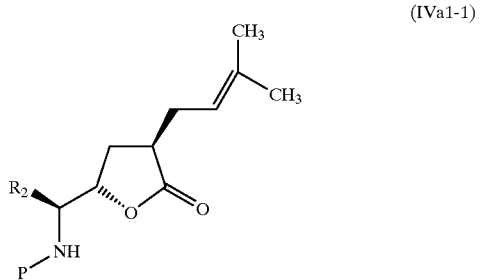
(IVa1-1)

wherein P is a protecting group, with phosphoric acid to form a compound of the formula (IIIa1-1)

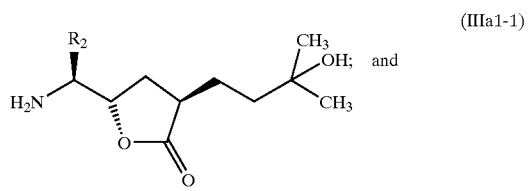
(IIIa1-1)

b) coupling the compound of the formula (IIIa1-1) so formed with a compound having the formula $R_1$—CO—X, wherein X is hydroxy or halogen.

3. A method of making a compound of the formula (Ia-1)

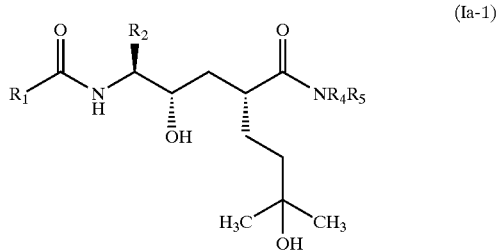
(Ia-1)

wherein:

$R_1$ is $(C_2-C_9)$heteroaryl optionally substituted with one, two or three substituents independently selected from the group consisting of hydrogen, halogen, cyano, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N(C=O)$—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl;

$R_2$ is phenyl-$(CH_2)_m$—, naphthyl-$(CH_2)_m$—, $(C_3-C_{10})$cycloalkyl-$(CH_2)_m$—, $(C_1-C_6)$alkyl or $(C_2-C_9)$heteroaryl-$(CH_2)_m$—, wherein each of said phenyl, naphthyl, $(C_3-C_{10})$cycloalkyl or $(C_2-C_9)$heteroaryl moieties of said phenyl-$(CH_2)_m$—, naphthyl-$(CH_2)_m$—, $(C_3-C_{10})$cycloalkyl-$(CH_2)_m$— or $(C_2-C_9)$heteroaryl-$(CH_2)_m$— groups may optionally be substituted with one, two, or three substituents independently selected from the group consisting of hydrogen, halogen, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N(C=O)$—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, phenoxy, benzyloxy, $(C_3-C_{10})$cycloalkyl, $(C_2-C_9)$heterocycloalkyl, and $(C_2-C_9)$heteroaryl;

$R_4$ is hydrogen, $(C_1-C_6)$alkyl, hydroxy, $(C_1-C_6)$alkoxy, hydroxy$(C_1-C_6)$alkyl, $(C_1-C_6)$alkoxy$(C=O)$—, $(C_3-C_{10})$cycloalkyl-$(CH_2)_q$—, $(C_2-C_6)$heterocycloalkyl-$(CH_2)_q$—, $(C_2-C_9)$heteroaryl-$(CH_2)_q$—, phenyl-$(CH_2)_q$—, or naphthyl-$(CH_2)_q$—; wherein said $(C_2-C_9)$heterocycloalkyl, $(C_2-C_9)$heteroaryl, phenyl and naphthyl groups may be optionally substituted with one or two substituents from the group consisting of hydrogen, halogen, cyano, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N(C=O)$—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, CF$_3$SO$_3$—, (C$_1$-C$_6$)alkyl-SO$_3$, phenyl, (C$_3$-C$_{10}$) cycloalkyl, (C$_2$-C$_9$)heterocycloalkyl, and (C$_2$-C$_9$) heteroaryl;

R$_5$ is hydrogen, (C$_1$-C$_6$)alkyl or amino; or

R$_4$ and R$_5$ together with the nitrogen atom to which they are attached form a (C$_2$-C$_9$)heterocycloalkyl group optionally substituted with one or two substituents selected from the group consisting of hydrogen, halogen, cyano, (C$_1$-C$_6$)alkyl, hydroxy, hydroxy-(C$_1$-C$_6$)alkyl, (C$_1$-C$_6$)alkoxy, (C$_1$-C$_6$)alkoxy(C$_1$-C$_6$)alkyl, HO—(C=O)—, (C$_1$-C$_6$)alkyl-O—(C=O)—, HO—(C=O)—(C$_1$-C$_6$)alkyl, (C$_1$-C$_6$)alkyl-O—(C=O)—(C$_1$-C$_6$)alkyl, (C$_1$-C$_6$)alkyl-(C=O)—O—, (C$_1$-C$_6$)alkyl-(C=O)—O—(C$_1$-C$_6$)alkyl, H(O=C)—, H(O=C)—(C$_1$-C$_6$)alkyl, (C$_1$-C$_6$)alkyl(O=C)—, (C$_1$-C$_6$)alkyl(O=C)—(C$_1$-C$_6$)alkyl, NO$_2$, amino, (C$_1$-C$_6$)alkylamino, [(C$_1$-C$_6$)alkyl]$_2$amino, amino(C$_1$-C$_6$)alkyl, (C$_1$-C$_6$)alkylamino (C$_1$-C$_6$)alkyl, [(C$_1$-C$_6$)alkyl]$_2$amino(C$_1$-C$_6$)alkyl, H$_2$N—(C=O)—, (C$_1$-C$_6$)alkyl-NH—(C=O)—, [(C$_1$-C$_6$)alkyl]$_2$N—(C=O)—, H$_2$N(C=O)—(C$_1$-C$_6$)alkyl, (C$_1$-C$_6$)alkyl-HN(C=O)—(C$_1$-C$_6$)alkyl, [(C$_1$-C$_6$)alkyl]$_2$N—(C=O)—(C$_1$-C$_6$)alkyl, H(O=C)—NH—, (C$_1$-C$_6$)alkyl(C=O)—NH, (C$_1$-C$_6$)alkyl(C=O)—[NH] (C$_1$-C$_6$)alkyl, (C$_1$-C$_6$)alkyl(C=O)—[N(C$_1$-C$_6$)alkyl] (C$_1$-C$_6$)alkyl, (C$_1$-C$_6$)alkyl-S—, (C$_1$-C$_6$)alkyl-(S=O)—, (C$_1$-C$_6$)alkyl-SO$_2$—, (C$_1$-C$_6$)alkyl-SO$_2$—NH—, H$_2$N—SO$_2$—, H$_2$N—SO$_2$—(C$_1$-C$_6$)alkyl, (C$_1$-C$_6$)alkylHN—SO$_2$—(C$_1$-C$_6$)alkyl, [(C$_1$-C$_6$)alkyl]$_2$N—SO$_2$—(C$_1$-C$_6$)alkyl, CF$_3$SO$_3$—, (C$_1$-C$_6$)alkyl-SO$_3$—, phenyl, (C$_3$-C$_{10}$)cycloalkyl, (C$_2$-C$_9$)heterocycloalkyl, and (C$_2$-C$_9$)heteroaryl;

m is 0, 1, 2, 3, or 4; and q is 0, 1, 2, 3, or 4;

wherein the method comprises:

a) reacting a compound of the formula (IVa1-1)

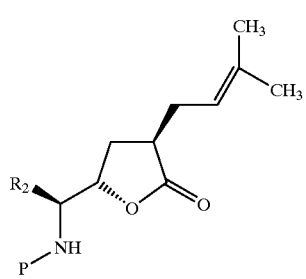

(IVa1-1)

wherein P is a protecting group, with phosphoric acid to form a compound of the formula (IIIa1-1)

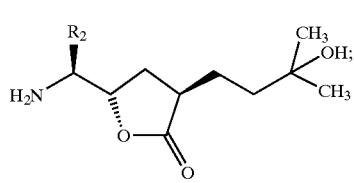

(IIIa1-1)

b) coupling the compound of the formula (IIIa1-1) so formed with a compound having the formula R$_1$—CO—X, wherein X is hydroxy or halogen, to form a compound of the formula (IIa1-1)

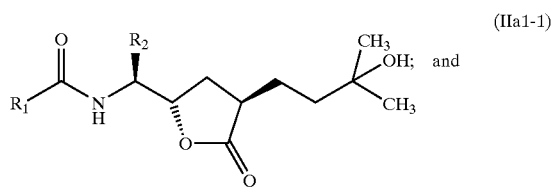

(IIa1-1)

c) reacting the compound of the formula (IIa1-1) so formed with an amine having a formula NHR$_4$R$_5$, wherein R$_4$ and R$_5$ are defined as above.

4. The method of any claims 1–3, wherein the compound of the formula (IVa1-1) is formed by reacting a compound of the formula (V-1)

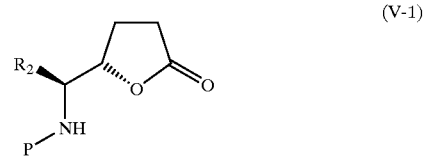

(V-1)

wherein P is a protecting group, with 4-halo-2-methyl-2-butene in the presence of a base.

5. The method of any claims 1–3, wherein R$_2$ is 3-fluorobenzyl.

6. The method of claim 2 or 3, wherein R$_1$ is quinoxaline.

7. The method of claim 3, wherein the compound of formula (Ia-1) is quinoxaline-2-carboxylic acid [4(R)-carbamoyl-1(S)-(3-fluoro-benzyl)-2(S),7-dihydroxy-7-methyl-octyl]-amide.

8. The method of any of claims 1–3, wherein the protecting group is carbobenzyloxy, t-butoxy carbonyl, or 9-fluorenyl-methylenoxy carbonyl.

9. The method of any claims 1–3, wherein the protecting group is t-butoxy carbonyl.

10. A compound of the formula (IIIa1-1):

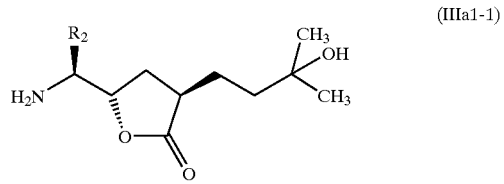

(IIIa1-1)

wherein:

R$_2$ is phenyl-(CH$_2$)$_m$—, naphthyl-(CH$_2$)$_m$—, (C$_3$-C$_{10}$) cycloalkyl-(CH$_2$)$_m$—, (C$_1$-C$_6$)alkyl or (C$_2$-C$_9$) heteroaryl-(CH$_2$)$_m$—, wherein each of said phenyl, naphthyl, (C$_3$-C$_{10}$)cycloalkyl or (C$_2$-C$_9$)heteroaryl moieties of said phenyl-(CH$_2$)$_m$—, naphthyl-(CH$_2$)$_m$—, (C$_3$-C$_{10}$)cycloalkyl-(CH$_2$)$_m$— or (C$_2$-C$_9$)heteroaryl-(CH$_2$)$_m$— groups may optionally be substituted with one, two, or three substituents independently selected from the group consisting of hydrogen, halogen, CN, (C$_1$-C$_6$)alkyl, hydroxy, hydroxy-(C$_1$-C$_6$)alkyl, (C$_1$-C$_6$)alkoxy, (C$_1$-C$_6$)alkoxy (C$_1$-C$_6$)alkyl, HO—(C=O)—, (C$_1$-C$_6$)alkyl-O—(C=O)—, HO—(C=O)—(C$_1$-C$_6$)alkyl, (C$_1$-C$_6$) alkyl-O—(C=O)—(C$_1$-C$_6$)alkyl, (C$_1$-C$_6$)alkyl-(C=O)—O—, (C$_1$-C$_6$)alkyl-(C=O)—O—(C$_1$-C$_6$) alkyl, H(O=C)—, H(O=C)—(C$_1$-C$_6$)alkyl, (C$_1$-C$_6$) alkyl(O=C)—, (C$_1$-C$_6$)alkyl(O=C)—(C$_1$-C$_6$)alkyl, NO$_2$, amino, (C$_1$-C$_6$)alkylamino, [(C$_1$-C$_6$)alkyl]$_2$ amino, amino $(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N-(C=O)-$, $(C_1-C_6)$alkyl-NH$-(C=O)-$, $[(C_1-C_6)$alkyl$]_2$N$-(C=O)-$, $H_2N(C=O)-(C_1-C_6)$alkyl, $(C_1-C_6)$alkyl-HN(C=O)$-(C_1-C_6)$alkyl, $[(C_1-C_6)$alkyl$]_2$N$-(C=O)-(C_1-C_6)$alkyl, $H(O=C)-NH-$, $(C_1-C_6)$alkyl$(C=O)-NH$, $(C_1-C_6)$alkyl$(C=O)-[NH](C_1-C_6)$alkyl, $(C_1-C_6)$alkyl$(C=O)-[N(C_1-C_6)$alkyl$](C_1-C_6)$alkyl, $(C_1-C_6)$alkyl-S$-$, $(C_1-C_6)$alkyl-$(S=O)-$, $(C_1-C_6)$alkyl-$SO_2-$, $(C_1-C_6)$alkyl-$SO_2-NH-$, $H_2N-SO_2-$, $H_2N-SO_2-(C_1-C_6)$alkyl, $(C_1-C_6)$alkylHN$-SO_2-(C_1-C_6)$alkyl, $[(C_1-C_6)$alkyl$]_2$N$-SO_2-(C_1-C_6)$alkyl, $CF_3SO_3-$, $(C_1-C_6)$alkyl-$SO_3-$, phenyl, phenoxy, benzyloxy, $(C_3-C_{10})$cycloalkyl, $(C_2-C_9)$heterocycloalkyl, and $(C_2-C_9)$heteroaryl;

m is 0, 1, 2, 3, or 4 and the salts and esters thereof.

11. The compound of claim 10, wherein $R_2$ is 3-fluorobenzyl.

* * * * *

UNITED STATES PATENT AND TRADEMARK OFFICE
CERTIFICATE OF CORRECTION

PATENT NO. : 6,858,744 B2
DATED : February 22, 2005
INVENTOR(S) : Kath et al.

It is certified that error appears in the above-identified patent and that said Letters Patent is hereby corrected as shown below:

<u>Title page,</u>
Item [54], Title, please replace "DIHYDOXYHEXANOIC" with
-- DIHYDROXYHEXANOIC --.

Signed and Sealed this

Thirty-first Day of May, 2005

JON W. DUDAS
*Director of the United States Patent and Trademark Office*